(12) United States Patent
Mullan et al.

(10) Patent No.: US 8,236,347 B2
(45) Date of Patent: Aug. 7, 2012

(54) PHARMACEUTICAL COMPOSITIONS FOR REDUCING AMYLOID DEPOSITION, AMYLOID NEUROTOXICITY, AND MICROGLIOSIS

(75) Inventors: Michael J. Mullan, Sarasota, FL (US); Daniel Paris, Sarasota, FL (US); Robert A. Ivey, III, Sarasota, FL (US)

(73) Assignee: Alzheimer's Institute of America, Inc., Kansas City, KS (US)

( * ) Notice: Subject to any disclaimer, the term of this patent is extended or adjusted under 35 U.S.C. 154(b) by 97 days.

(21) Appl. No.: 12/697,436

(22) Filed: Feb. 1, 2010

(65) Prior Publication Data

US 2010/0183711 A1   Jul. 22, 2010

Related U.S. Application Data

(62) Division of application No. 12/245,354, filed on Oct. 3, 2008.

(60) Provisional application No. 60/977,953, filed on Oct. 5, 2007, provisional application No. 61/046,109, filed on Apr. 18, 2008.

(51) Int. Cl.
*A61K 9/64* (2006.01)
*A61K 31/44* (2006.01)

(52) U.S. Cl. .................. 424/456; 514/355; 514/356

(58) Field of Classification Search .................. None
See application file for complete search history.

(56) References Cited

U.S. PATENT DOCUMENTS

| | | |
|---|---|---|
| 4,338,322 A | 7/1982 | Sato |
| 4,654,206 A | 3/1987 | Okuda et al. |
| 4,820,720 A | 4/1989 | Sanders et al. |
| 4,859,688 A | 8/1989 | Yamaguchi et al. |
| 4,902,514 A | 2/1990 | Barclay et al. |
| 4,992,445 A | 2/1991 | Lawter et al. |
| 5,001,139 A | 3/1991 | Lawter et al. |
| 5,045,553 A | 9/1991 | Ueda et al. |
| 5,053,419 A | 10/1991 | Lipton |
| 5,114,946 A | 5/1992 | Lawter et al. |
| 5,160,734 A | 11/1992 | Ganesan et al. |
| 5,258,393 A | 11/1993 | Nakashima et al. |

(Continued)

FOREIGN PATENT DOCUMENTS

DE     4141646 A1    6/1993

(Continued)

OTHER PUBLICATIONS

Maxwell et al., "Calcium-channel blockers and cognitive function in elderly people; results from the Canadian Study of Health and Aging," CMAJ 161(5): 501-506, 1999.

(Continued)

*Primary Examiner* — Robert A Wax
*Assistant Examiner* — Jeffrey T Palenik
(74) *Attorney, Agent, or Firm* — Bryan Cave LLP

(57) ABSTRACT

The present invention provides methods for reducing Aβ deposition, Aβ neurotoxicity and microgliosis in an animal or human afflicted with a cerebral amyloidogenic disease, such as Alzheimer's disease (AD), by administering therapeutically effective amounts of the (R)-enantiomer of the dihydropyridine compound nilvadipine, also known as (−)-nilvadipine, to the animal or human. Further provided are methods for reducing the risk of Aβ deposition, Aβ neurotoxicity and microgliosis in animals or humans suffering from traumatic brain injury by administering (−)-nilvadipine after the traumatic brain injury and continuing treatment for a prescribed period of time thereafter.

8 Claims, 18 Drawing Sheets

U.S. PATENT DOCUMENTS

| | | | |
|---|---|---|---|
| 5,340,591 | A | 8/1994 | Nakano et al. |
| 5,508,413 | A | 4/1996 | Shiokawa et al. |
| 5,683,716 | A * | 11/1997 | Hata et al. ............ 424/451 |
| 5,834,496 | A | 11/1998 | Young |
| 6,271,259 | B1 | 8/2001 | Kakuda et al. |
| 6,294,544 | B1 | 9/2001 | Araie et al. |
| 6,420,405 | B2 | 7/2002 | Inada et al. |
| 6,818,200 | B2 | 11/2004 | Foster et al. |
| 2001/0011098 | A1 | 8/2001 | Inada et al. |
| 2002/0042405 | A1 | 4/2002 | Schuh |
| 2002/0094995 | A1 | 7/2002 | Foster et al. |
| 2002/0115655 | A1 | 8/2002 | Mehanna et al. |
| 2003/0013699 | A1 | 1/2003 | Davis et al. |
| 2003/0044845 | A1 | 3/2003 | Jenkins et al. |
| 2003/0055027 | A1 | 3/2003 | Schun |
| 2003/0139801 | A1 | 7/2003 | Sirhan et al. |
| 2004/0063730 | A1 | 4/2004 | Eggenweiler et al. |
| 2004/0072846 | A1 | 4/2004 | Eggenweiler et al. |
| 2004/0101517 | A1 | 5/2004 | Bolton et al. |
| 2004/0242565 | A1 | 12/2004 | Toshima et al. |
| 2005/0009885 | A1 | 1/2005 | Mullan et al. |
| 2005/0031651 | A1 | 2/2005 | Gervais et al. |

FOREIGN PATENT DOCUMENTS

| | | |
|---|---|---|
| DE | 42 29 805 A1 | 3/1994 |
| EP | 0 294 601 A2 | 12/1988 |
| EP | 0 301 133 A2 | 2/1989 |
| EP | 0 317 780 A1 | 5/1989 |
| EP | 0 628 313 A1 | 12/1994 |
| EP | 1 260 232 A1 | 11/2002 |
| EP | 1 285 655 A1 | 2/2003 |
| JP | 61129140 A2 | 6/1986 |
| JP | 02117658 A2 | 5/1990 |
| JP | 03099061 A2 | 4/1991 |
| JP | 03081262 | 5/1991 |
| JP | 03123730 A2 | 5/1991 |
| JP | 05139974 A2 | 6/1993 |
| JP | 2001335483 A2 | 12/2001 |
| JP | 2002087959 A2 | 3/2002 |
| JP | 2002097140 A2 | 4/2002 |
| JP | 2003146878 A2 | 5/2003 |
| JP | 03470096 B2 | 11/2003 |
| JP | 2004002460 A2 | 1/2004 |
| KR | 0222306 B1 | 10/1999 |
| WO | 92/03137 A1 | 3/1992 |
| WO | 93/05770 A1 | 1/1993 |
| WO | 99/63992 A1 | 12/1999 |
| WO | 99/64045 A1 | 12/1999 |
| WO | 00/02543 A2 | 1/2000 |
| WO | 02/060461 A | 8/2002 |
| WO | 02/096415 A2 | 12/2002 |
| WO | 03/097045 A1 | 11/2003 |
| WO | 03/097067 A1 | 11/2003 |
| WO | 03/097098 A1 | 11/2003 |
| WO | 2004 034963 A2 | 4/2004 |
| WO | 2004/058258 A | 7/2004 |

OTHER PUBLICATIONS

Meredith and Elliot, "Dihydropyridine calcium channel blockers: basic pharmacological similarities but fundamental therapeutic differences," J Hypertens 22:1641-1648, 2004.

Yamada et al., "Alterations in calcium antagonist receptors and calcium content in senescent brain and attenuation by nimodipine and nicardipine," JPET 277:721-727, 1996.

McGeer, Patrick L., and Edith G. McGeer, "Inflammation of the brain in Alzheimer's disease: implications for therapy," Journal of Leukocyte Biology, Apr. 1999, vol. 65: 409-415.

Nilsson, Lars N. G., et al., "Alpha-1-Antichymotrypsin Promotes Beta-Sheet Amyloid Plague Deposition in a Transgenic Mouse Model of Alzheimer's Disease," The Journal of Neuroscience, Mar. 2001, 21(5): 1444-1451.

Strupp, Prof. Dr. Med. "Recent treatment studies in Alzheimer's disease, MS, cluster headache, focal cortical dysplasia and ALS," J. Neurol. 251:1546-1548, (2004).

International Search Report for PCT/US08/78786 dated Dec. 16, 2008.

International Search Report for PCT/2004/015417 dated Dec. 23, 2004.

International Search Report for PCT/2008/078803 dated Dec. 17, 2008.

Furuichi et al., "The Effect of Nilvadipine, a Dihydropyridine Type Calcium Channel Blocker, on Local Cerebral Blood Flow in Rats," Japan J. Pharmacol. 58:457-460, 1992.

Cahn, R.S., "Errata: An Introduction to the Sequence Rule," J. Chem. Educ., 1964, vol. 41, p. 508.

Ebiike et al., "Lipase-catalyzed Asymmetric Hydrolysis and Regioselective Bromination of 1,4-Dihydropyridine. Synthesis of (R)-(+)-Nilvadipine," Tetrahedron: Asymmetry, 1994, vol. 5, No. 8, pp. 1447-1450.

Nakagawa et al., "Disposition of Dihydropyridine Series Calcium Antagonist Nilvadipine (IX) Optical Isomer Drug Interaction Disposition after Oral Administration in Dogs," Pharmacokinetics, 1988, vol. 3, No. 5, pp. 108-109 (including English translation).

Satoh et al., "Studies on Nilvadipine. IV. Sythesis of Deuteriated and Optically Active Isopropyl 2-Cyano-3-methoxycarbonyl-4-(3-nitrophenyl)-6-methyl-1,4-dihydropyridine-5-carboxylate (Nilvadipine)," Chem. Pharm. Bull., 1994, vol. 42, No. 4, pp. 950-952.

Tokuma et al., "Stereoselective pharmacokinetics of dihydropyridine calcium antagonists," J. Chromat., 1995, vol. 694, pp. 181-193.

* cited by examiner

PHARMACEUTICAL COMPOSITIONS FOR REDUCING AMYLOID DEPOSITION, AMYLOID NEUROTOXICITY, AND MICROGLIOSIS

CROSS-REFERENCE TO RELATED APPLICATIONS

This application is a divisional of U.S. Ser. No. 12/245,354, filed Oct. 3, 2008, which claims priority to U.S. Provisional Application Ser. No. 60/977,953, filed Oct. 5, 2007, and U.S. Provisional Application Ser. No. 61/046,109, filed Apr. 18, 2008, each of which is incorporated herein by reference in its entirety.

BACKGROUND OF THE INVENTION

1. Field of the Invention

The present invention relates to a method for treating the pathophysiological effects of cerebral amyloidogenic diseases, such as Alzheimer's disease. More specifically, the method involves administering the (−) enantiomer of nilvadipine to oppose pathophysiological effects in the brain of animals or humans afflicted with diseases associated with cerebral amyloidosis, such as Alzheimer's disease, with reduced antihypertensive side effects compared to the racemic mixture of nilvadipine.

2. Description of Related Art

Alzheimer's disease (AD) is the most common neurodegenerative disorder of aging, afflicting approximately 1% of the population over the age of 65. Characteristic features of the disease include the progressive accumulation of intracellular neurofibrillary tangles, extracellular parenchymal senile plaques, and cerebrovascular deposits in the brain. The principal component of senile plaques and cerebrovascular deposits is the 39-43 amino acid β-amyloid peptide (Aβ), which is proteolytically derived from amyloid precursor protein (APP), a transmembrane glycoprotein.

APP is a single-transmembrane protein with a 590-680 amino acid extracellular amino terminal domain and an approximately 55 amino acid cytoplasmic tail. Messenger RNA from the APP gene on chromosome 21 undergoes alternative splicing to yield eight possible isoforms, three of which (the 695, 751 and 770 amino acid isoforms) predominate in the brain. APP undergoes proteolytic processing via three enzymatic activities, termed α-, β- and γ-secretase. Alpha-secretase cleaves APP at amino acid 17 of the Aβ domain, thus releasing the large soluble amino-terminal fragment α-APP for secretion. Because α-secretase cleaves within the Aβ domain, this cleavage precludes Aβ formation. Alternatively, APP can be cleaved by β-secretase to define the amino terminus of Aβ and to generate the soluble amino-terminal fragment β-APP. Subsequent cleavage of the intracellular carboxy-terminal domain of APP by γ-secretase results in the generation of multiple peptides, the two most common being 40-amino acid Aβ (Aβ40) and 42-amino acid Aβ (Aβ42). Aβ40 comprises 90-95% of the secreted Aβ and is the predominant species recovered from cerebrospinal fluid (Seubert et al., Nature, 359:325-7, 1992). In contrast, less than 10% of secreted Aβ is Aβ42. Despite the relative paucity of Aβ42 production, Aβ42 is the predominant species found in plaques and is deposited initially, perhaps due to its ability to form insoluble amyloid aggregates more rapidly than Aβ40 (Jarrett et al., Biochemistry, 32:4693-7, 1993). The abnormal accumulation of Aβ in the brain is believed due to either over-expression or altered processing of APP.

Aβ peptides are thus believed to play a critical role in the pathobiology of AD, as all the mutations associated with the familial form of AD result in altered processing of these peptides from APP. Indeed, deposits of insoluble, or aggregated, fibrils of Aβ in the brain are a prominent neuropathological feature of all forms of AD, regardless of the genetic predisposition of the subject.

Concomitant with Aβ deposition, there exists robust activation of inflammatory pathways in AD brain, including production of pro-inflammatory cytokines and acute-phase reactants in and around Aβ deposits (McGeer et al., J Leukocyte Biol., 65:409-15, 1999). Activation of the brain's resident innate immune cells, the microglia, is thought to be intimately involved in this inflammatory cascade. It has been demonstrated that reactive microglia produce pro-inflammatory cytokines, such as inflammatory proteins and acute phase reactants, such as alpha-1-antichymotrypsin, transforming growth factor β, apolipoprotein E and complement factors, all of which have been shown to be localized to Aβ plaques and to promote Aβ plaque "condensation" or maturation (Nilsson et al., J. Neurosci. 21:1444-5, 2001), and which at high levels promote neurodegeneration. Epidemiological studies have shown that patients using non-steroidal anti-inflammatory drugs (NSAIDS) have as much as a 50% reduced risk for AD (Rogers et al., Neurobiol. Aging 17:681-6, 1996), and post-mortem evaluation of AD patients who underwent NSAID treatment has demonstrated that risk reduction is associated with diminished numbers of activated microglia (Mackenzie et al., Neurology 50:986-90, 1998). Further, when Tg APP$_{sw}$ mice, a mouse model for Alzheimer's disease, are given an NSAID (ibuprofen), these animals show reduction in Aβ deposits, astrocytosis, and dystrophic neuritis correlating with decreased microglial activation (Lim et al., J. Neurosci. 20:5709-14, 2000).

Products of the inflammatory process in the AD brain therefore may exacerbate AD pathology. Furthermore, there is evidence that activated microglia in AD brain, instead of clearing Aβ, are pathogenic by promoting Aβ fibrillogenesis and consequent deposition as senile plaques (Wegiel et al., Acta Neuropathol. (Berl.) 100:356-64, 2000).

It also has been suggested that AD pathogenesis is due to the neurotoxic properties of Aβ. The cytotoxicity of Aβ was first established in primary cell cultures from rodent brains and also in human cell cultures. The work of Mattson et al. (J. Neurosci., 12:376-389, 1992) indicates that Aβ, in the presence of the excitatory neurotransmitter glutamate, causes an immediate pathological increase in intracellular calcium, which is believed to be very toxic to the cell through its greatly increased second messenger activities.

U.S. Patent Application No. 2005/0009885 (Jan. 13, 2005) (Mullan et al.) discloses a method for reducing Aβ deposition using nilvadipine, as well as methods of diagnosing cerebral amyloidogenic diseases using nilvadipine. However, U.S. Pat. No. 4,338,322 describes nilvadipine for its antihypertensive effects. Nilvadipine (NIVADIL™) has received regulatory approval in Ireland for treatment of hypertension at a dose of 8 mg per day, or 16 mg per day if an adequate anti-hypertensive effect is not achieved with 8 mg per day. See also U.S. Pat. No. 5,508,413, which discloses antihypertensive effects of the (+)-enantiomer of nilvadipine. Racemic nilvadipine and its effect on regional cerebral blood flow in human subjects are reported in Hanyu et al. (Nuclear Medicine Communications, vol. 28, no. 4, pages 281-287, April 2007).

Despite the reports indicated above, there exists a need for a prophylaxis for the inexorable progression of brain degeneration that is a hallmark of AD, wherein the prophylaxis addresses the Aβ deposition, Aβ neurotoxicity, microglial-activated inflammation, and altered or overexpression of APP that is seen in AD patients with therapeutically effective treatment with minimal side effects such as unwanted or excessive reduction in blood pressure.

SUMMARY OF THE INVENTION

In order to meet this need, the present invention provides methods for reducing Aβ deposition, Aβ neurotoxicity and microgliosis in an animal or human afflicted with a cerebral amyloidogenic disease, such as Alzheimer's disease (AD), by administering to the animal or human therapeutically effective amounts of enantiomerically-enriched (−)-nilvadipine. In particular, the present invention provides for administration of enantiomerically-enriched (−)-nilvadipine with a reduced hypotensive effect compared to the same amount of racemic nilvadipine. In addition, administration of enantiomerically-enriched (−)-nilvadipine permits increased dosages compared to administration of racemic nilvadipine or (+)-nilvadipine due to a reduction in hypotensive effect. For example, the data presented herein demonstrates baseline aortic contraction when challenged with FPL64176 for the (−)-enantiomer, which correlates with reduced vasoactivity for the (−)-enantiomer compared to the racemic mixture or (+)-enantiomer which exhibit vasoactivity (i.e., antagonism of induced vasoconstriction). In preferred embodiments, the (−)-enantiomer is present in excess in the administered composition, and the enantiomeric excess is preferably 90% or more, 95% or more, and more preferably 98% or more, including 100%, up to the detectable limit of purity.

The present invention further provides methods for reducing the risk of Aβ deposition, Aβ neurotoxicity and microgliosis in animals or humans suffering from traumatic brain injury by administering to the animal or human a therapeutically effective amount of enantiomerically-enriched (−)-nilvadipine after the head injury and continuing enantiomerically-enriched (−)-nilvadipine treatment for a prescribed period of time thereafter. In particular, the present invention provides for administration of enantiomerically-enriched (−)-nilvadipine with a reduced hypotensive effect compared to the same amount of racemic nilvadipine. In addition, administration of enantiomerically-enriched (−)-nilvadipine permits increased dosages compared to administration of racemic nilvadipine due to a reduction in hypotensive effect. In preferred embodiments, the (−)-enantiomer is present in excess in the administered composition, and the enantiomeric excess is preferably 90% or more, 95% or more, and more preferably 98% or more, including 100%, up to the detectable limit of purity.

The present invention also provides for methods for reducing the risk of developing, or slowing the onset or progression of, or of stabilizing the symptoms of, a cerebral amyloidogenic disease or condition in animals and humans diagnosed with a risk for developing cerebral amyloidogenic disease or condition, comprising administering to the animal or human a therapeutically effective amount of enantiomerically-enriched (−)-nilvadipine, wherein the enantiomerically-enriched (−)-nilvadipine administration begins after the diagnosis of risk for developing cerebral amyloidogenic disease or condition. In particular, the present invention provides for administration of enantiomerically-enriched (−)-nilvadipine with a reduced hypotensive effect compared to the same amount of racemic nilvadipine. In addition, administration of enantiomerically-enriched (−)-nilvadipine permits increased dosages compared to administration of racemic nilvadipine due to a reduction in hypotensive effect. In preferred embodiments, the (−)-enantiomer is present in excess in the administered composition, and the enantiomeric excess is preferably 90% or more, 95% or more, and more preferably 98% or more, including 100%, up to the detectable limit of purity.

The present invention provides for treating the clinical profile of a cerebral amyloidogenic disease encompassing one or more or all of the cognitive and behavioral traits associated with the cerebral amyloidogenic disease. For example, with regard to AD, such traits may include a non-limiting list of symptoms such as profound memory loss, difficulty in performing familiar tasks, problems with language, disorientation, decreased judgment, impaired abstract thinking, changes in personality, mood, or behavior, and/or characteristic scores in a battery of cognitive tests. Such cognitive tests include the Wechsler Memory Scale Revised (WMS-R), the Clinical Dementia Rating (CDR), the Mini-Mental State Examination (MMSE) and/or the Alzheimer's Disease Assessment Scale-Cognitive Subscale (ADAS).

The present invention provides for treatment with enantiomerically-enriched (−)-nilvadipine which may yield a specific clinical outcome. One endpoint for treatment is a measurable improvement in one or more disease symptoms in those affected by cerebral amyloidogenic disease. The improvement may result in an asymptomatic patient, or may reflect an improvement in ability compared to one or more symptoms prior to treatment. Alternatively, one endpoint for treatment may be to maintain a baseline symptomatic level. In other words, this endpoint represents stabilization of the disease or one or more symptoms of the disease permanently or for a period of time. In addition, one endpoint for treatment may be a reduction in the rate of disease progression compared to an untreated control. Furthermore, treatment may include pretreatment of an individual considered to be at risk for development of cerebral amyloidogenic disease, but prior to clinical manifestation of one or more symptoms. Reference to treatment of disease also encompasses treatment of one or more symptoms, where the treatment is palliative rather than curative.

The present invention also provides methods for treating transplantable neuronal stem cells, comprising administering an amount of enantiomerically-enriched (−)-nilvadipine to the neuronal stem cells prior to transplantation of the stem cells in the central nervous system of an animal or human afflicted with a cerebral amyloidogenic disease, such as AD. The administered amount is the amount that achieves the desired cytoprotective effect. In preferred embodiments, the (−)-enantiomer is present in excess in the administered composition, and the enantiomeric excess is preferably 90% or more, 95% or more, and more preferably 98% or more, including 100%, up to the detectable limit of purity.

DESCRIPTION OF THE PREFERRED EMBODIMENTS

Figure 1:
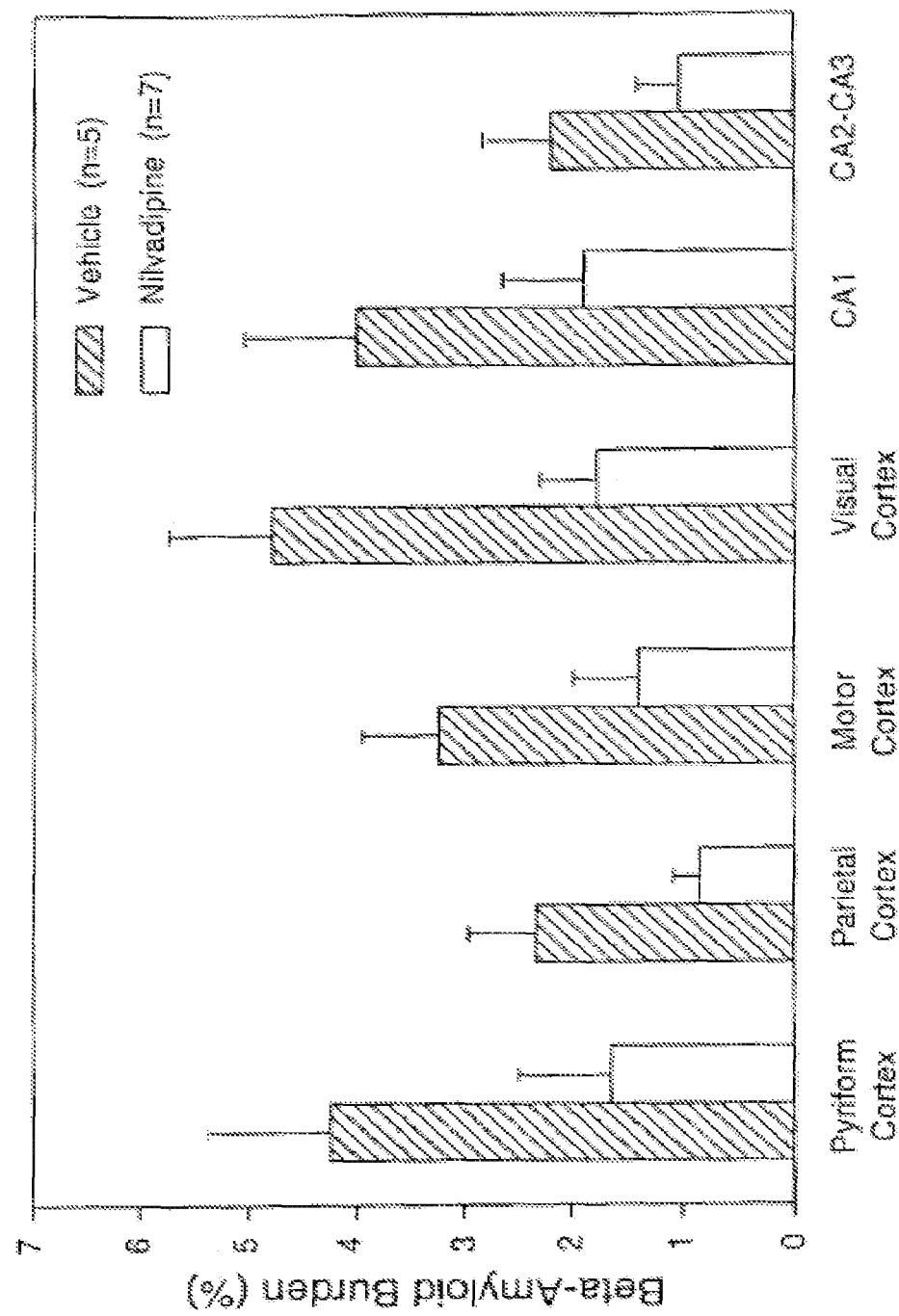
FIG. 1 is a bar graph that illustrates the effect of chronic administration of nilvadipine on Aβ deposition (Aβ burden) in different regions of the brain of TgAPP$_{sw}$ mice using a 4G8 immunostaining technique.

The present invention provides prophylactic methods and therapeutic methods for addressing the inexorable progression of brain degeneration that is a hallmark of certain cerebral amyloidogenic diseases, such as, Alzheimer's disease (AD), in animals and humans, by administering enantiomerically-enriched (−)-nilvadipine (isopropyl-3-methyl-2-cyano-1,4-dihydro-6-methyl-4-(m-nitrophenyl)-3,5-pyridine-dicarboxylate; MW 385.4). Treatment, prevention, and amelioration of symptoms are encompassed by methods according to the invention.

Unless otherwise specified, the term nilvadipine as used herein refers to the racemic mixture. The term "enantiomerically enriched" as used herein, refers to a compound that is a mixture of enantiomers in which the (−)-enantiomer is present in excess, and preferably present to the extent of 90% or more, 95% or more, and more preferably 98% or more, including 100%, up to the detectable limit of purity. For example, purity can be determined by detection with chiral HPLC methods. In one embodiment, enantiomeric excess is calculated by subtracting the minor component from the major component. For example, a mixture of enantiomers with 98% (−)-enantiomer and 2% (+)-enantiomer would be calculated as a 96% enantiomeric excess of the (−)-enantiomer.

In particular, one embodiment of the present invention provides a method for reducing Aβ-deposition, Aβ neurotoxicity and microgliosis in an animal or human afflicted with a cerebral amyloidogenic disease or condition by administering therapeutically effective amounts of enantiomerically-enriched (−)-nilvadipine to the animal or human. Because most cerebral amyloidogenic diseases, such as AD, are chronic, progressive, intractable brain dementias, it is contemplated that the duration of enantiomerically-enriched (−)-nilvadipine treatment will last for up to the lifetime of the animal or human. The cerebral amyloidogenic diseases or conditions include without limitation Alzheimer's disease, traumatic brain injury, and cerebral amyloid angiopathy.

In another embodiment, the present invention provides a method for treating transmissible spongiform encephalopathy, scrapie, or Gerstmann-Straussler-Scheinker syndrome.

In another embodiment of the present invention, a method is provided for reducing the risk of Aβ deposition, Aβ neurotoxicity and microgliosis in animals or humans suffering from traumatic brain injury (TBI) by administering to the animal or human a therapeutically effective amount of enantiomerically-enriched (−)-nilvadipine after the TBI and continuing the enantiomerically-enriched (−)-nilvadipine treatment for a prescribed period of time thereafter. The duration of enantiomerically-enriched (−)-nilvadipine treatment that is contemplated for those animals or humans suffering from a TBI can last for between about one hour to five years, preferably between about two weeks to three years, and most preferably between about six months and twelve months.

In another embodiment, a method is provided for treating the clinical profile of a cerebral amyloidogenic disease encompassing one or more or all of the cognitive and behavioral traits associated with the cerebral amyloidogenic disease. For example, with regard to AD, such traits may include a non-limiting list of symptoms such as profound memory loss, difficulty in performing familiar tasks, problems with language, disorientation, decreased judgment, impaired abstract thinking, changes in personality, mood, or behavior, and/or characteristic scores in a battery of cognitive tests. Such cognitive tests include the Wechsler Memory Scale Revised (WMS-R), the Clinical Dementia Rating (CDR), the Mini-Mental State Examination (MMSE) and/or the Alzheimer's Disease Assessment Scale-Cognitive Subscale (ADAS).

In one or more embodiments, treatment with enantiomerically-enriched (−)-nilvadipine may yield a specific clinical outcome. One endpoint for treatment is a measurable improvement in one or more disease symptoms in those affected by cerebral amyloidogenic disease. The improvement may result in an asymptomatic patient, or may reflect an improvement in ability compared to one or more symptoms prior to treatment. Alternatively, one endpoint for treatment may be to maintain a baseline symptomatic level. In other words, this endpoint represents stabilization of the disease or one or more symptoms of the disease permanently or for a period of time. In addition, one endpoint for treatment may be a reduction in the rate of disease progression compared to an untreated control. Furthermore, treatment may include pre-treatment of an individual considered to be at risk for development of cerebral amyloidogenic disease, but prior to clinical manifestation of one or more symptoms. Reference to treatment of disease also encompasses treatment of one or more symptoms, where the treatment is palliative rather than curative.

The therapeutically effective amount of enantiomerically-enriched (−)-nilvadipine that is administered, optionally in unit dosage form, to animals or humans afflicted with a cerebral amyloidogenic disease or suffering from a traumatic brain injury, as well as administered for the purpose of determining the risk of developing and/or a diagnosis of a cerebral amyloidogenic disease in an animal or human, according to the methods of the present invention, can range from between about 0.05 mg to 20 mg per day, preferably from between about 2 mg to 15 mg per day, more preferably from between about 4 mg to 12 mg per day, and most preferably about 8 mg per day. The daily dosage can be administered in a single unit dose or divided into two, three or four unit doses per day. In another embodiment, the therapeutically effective amount of enantiomerically-enriched (−)-nilvadipine is greater than 16 mg per day up to the limit of the maximum tolerated dose. For example, the therapeutically effective amount of enantiomerically-enriched (−)-nilvadipine can range from 16 mg per to about 20 mg per day. Alternatively, the therapeutically effective amount of enantiomerically-enriched (−)-nilvadipine can be about 20 mg per day, about 30 mg per day, about 40 mg per day, about 50 mg per day, about 75 mg per day, about 100 mg per day, about 125 mg per day, about 150 mg per day, about 175 mg per day, about 200 mg per day, about 225 mg per day, about 250 mg per day, about 275 mg per day, about 300 mg per day, about 325 mg per day, about 350 mg per day, about 375 mg per day, about 400 mg per day, about 425 mg per day, about 450 mg per day, about 475 mg per day, about 500 mg per day, or up to the maximum tolerated dose per day, and any amount, integer or otherwise, between the foregoing amounts. Ranges can vary. For example, non-limiting ranges include lower endpoints of 20, 40, 60, 80, or 100 mg per day, and upper endpoints of 50, 100, 150, 200, 250, 300, and 500 mg per day, and any amount integer or otherwise, within the above mentioned amounts can serve as an endpoint.

While not wishing to be bound by theory, it is believed that anti-hypertensive effects may limit the maximum tolerated amount of racemic nilvadipine. In one embodiment according to the invention, the therapeutically effective amount of enantiomerically-enriched (−)-nilvadipine reduces blood pressure by an amount selected from the group consisting of less than about 30%, less than about 20%, less than about 10%, less than about 5%, and less than about 1%, of the pretreatment blood pressure following administration of the enantiomerically-enriched (−)-nilvadipine. Blood pressure can be measured in a variety of ways. For example, blood pressure can be measured as a systolic pressure or a diastolic pressure in millimeters of mercury.

Alternatively, blood pressure can be calculated according to the formula of ⅔ diastolic plus ⅓ systolic pressure readings. In one embodiment, the blood pressure is monitored continuously and integrated over time to give a single value for the area under the curve (AUC). The change in blood pressure may be in comparison to the normal population, or may be in comparison to the treated individual's pre-treatment blood pressure. In one embodiment, the post-treatment blood pressure is measured after a period of treatment such that a steady-state change in blood pressure has been established. For example, post-treatment blood pressure may be measured after about 1 week of treatment, about 4 weeks of treatment, about 12 weeks of treatment, about 6 months of treatment, and the like. In one embodiment, the enantiomerically-enriched (−)-nilvadipine is administered to a human or animal that has normal blood pressure, or is hypotensive. In one embodiment, the enantiomerically-enriched (−)-nilvadipine is administered to a human or animal that is hypertensive. In humans, normal blood pressure is considered to be between about 90/50 mm Hg to about 135/90 mm Hg. Blood pressure in humans below the normal range is considered hypotensive.

In another embodiment, the therapeutic of the invention is administered to patients that are hypertensive or to patients regardless of their blood pressure levels. Hypertensive patients may be concurrently treated with an anti-hypertensive. Blood pressure in humans above the normal range is considered hypertensive.

Normal ranges for various animals can be found in standard veterinary handbooks. In one embodiment, blood pressure is in the normal range either naturally or due to medical intervention, such as administration of an additional anti-hypertensive agent.

In still another embodiment of the present invention is a method for pre-treating transplantable human or xenogenic neuronal stem cells by administering a therapeutically effective amount of enantiomerically-enriched (−)-nilvadipine to the neuronal stem cells prior to transplantation of the cells in the central nervous system of an animal or human that may be afflicted with a cerebral amyloidogenic disease, such as AD. Presumably, neuronal stem cells themselves would not have a significant deposition of Aβ. However, if the neuronal transplant is intended for an Aβ-burdened environment, pre-treatment of the neuronal stem cells should enhance the ability of the transplanted neurons to survive in their new environment by reducing the Aβ concentration and thus the Aβ-toxicity therein. The therapeutically effective amount of enantiomerically-enriched (−)-nilvadipine that is administered for pre-treating the neuronal stem cells can range from between about 1 nM to 3 µM, preferably between about 10 nM to 2 and most preferably between about 100 nM to 1 µM. It is known that stem cells, when directed to differentiate into specific cell types, such as neuronal cells, offer the possibility of a renewable source of replacement cells and tissues to treat diseases and conditions, such Alzheimer's disease, Parkinson's disease or spinal cord injury. When such cells are transplanted/implanted into a patient, it is advisable not only to pre-treat the cells with enantiomerically-enriched (−)-nilvadipine but to begin therapeutic treatment of the patient with enantiomerically-enriched (−)-nilvadipine post-implantation as well.

It is contemplated that the methods of the present invention may be tested on known transgenic animal models for AD, such as the PDAPP and TgAPP$_{sw}$ mouse models prior to testing for efficacy in treating, preventing and/or inhibiting conditions associated with amyloid deposition, Aβ neurotoxicity and microgliosis in the central nervous system of humans. Such transgenic animal models for AD are constructed using standard methods known in the art and, for example, as set forth in U.S. Pat. Nos. 5,487,992; 5,464,764; 5,387,742; 5,360,735; 5,347,075; 5,298,422; 5,288,846; 5,221,778; 5,175,385; 5,175,384; 5,175,383; and 4,736,866.

Enantiomerically-enriched (−)-nilvadipine can be administered to a patient via various routes including parenterally, orally or intraperitoneally. Parenteral administration includes the following routes: intravenous; intramuscular; interstitial; intra-arterial; subcutaneous; intraocular; intracranial; intrathecal; intraventricular; intrasynovial; transepithelial, including transdermal, pulmonary via inhalation, ophthalmic, sublingual and buccal; topical, including ophthalmic, dermal, ocular, rectal, or nasal inhalation via insufflation or nebulization.

Enantiomerically-enriched (−)-nilvadipine that is orally administered can be enclosed in hard or soft shell gelatin capsules, or compressed into tablets. Enantiomerically-enriched (−)-nilvadipine also can be incorporated with an excipient and used in the form of ingestible tablets, buccal tablets, troches, capsules, sachets, lozenges, elixirs, suspensions, syrups, wafers, and the like. Further, enantiomerically-enriched (−)-nilvadipine can be in the form of a powder or granule, a solution or suspension in an aqueous liquid or non-aqueous liquid, or in an oil-in-water or water-in-oil emulsion.

The tablets, troches, pills, capsules and the like also can contain, for example, a binder, such as gum tragacanth, acacia, corn starch; gelating excipients, such as dicalcium phosphate; a disintegrating agent, such as corn starch, potato starch, alginic acid and the like; a lubricant, such as magnesium stearate; a sweetening agent, such as sucrose, lactose or saccharin; or a flavoring agent. The active ingredient may be formulated or administered in a unit dosage form or in a non-unit dosage form. When the dosage unit form is a capsule, it can contain, in addition to the materials described above, a liquid carrier. Various other materials can be present as coatings or to otherwise modify the physical form of the dosage unit. For example, tablets, pills, or capsules can be coated with shellac, sugar or both. A syrup or elixir can contain nilvadipine, sucrose as a sweetening agent, methyl and propylparabens as preservatives, a dye and flavoring. Additionally, enantiomerically-enriched (−)-nilvadipine can be incorporated into sustained-release preparations and formulations.

Enantiomerically-enriched (−)-nilvadipine can be administered to the CNS, parenterally or intraperitoneally. Solutions of nilvadipine as a free base or a pharmaceutically acceptable salt can be prepared in water mixed with a suitable surfactant, such as hydroxypropylcellulose. Dispersions also can be prepared in glycerol, liquid polyethylene glycols, and mixtures thereof, and in oils. Under ordinary conditions of storage and use, these preparations can contain a preservative and/or antioxidants to prevent the growth of microorganisms or chemical degeneration.

The desired (−)-nilvadipine enantiomer has the (S) configuration at its chiral center. The compound provided herein may be enantiomerically pure, or be a stereoisomeric mixture with some amount of (+)(R)-nilvadipine. It is understood that the disclosure of enantiomerically-enriched (−)-nilvadipine herein encompasses any optically active, polymorphic, or stereoisomeric form, or mixtures thereof, which preferably possesses the useful properties described herein, it being well known in the art how to prepare optically active forms and how to determine activity using the standard tests described herein, or using other similar tests which are will known in the art. The term "enantiomerically enriched" as used herein, refers to a compound that is a mixture of enantiomers in which the (−)-enantiomer is present in excess, and preferably present to the extent of 90% or more, 95% or more, and more preferably 98% or more, including 100%, up to the detectable limit of purity. For example, purity can be determined by detection with chiral HPLC methods.

Figure 8:
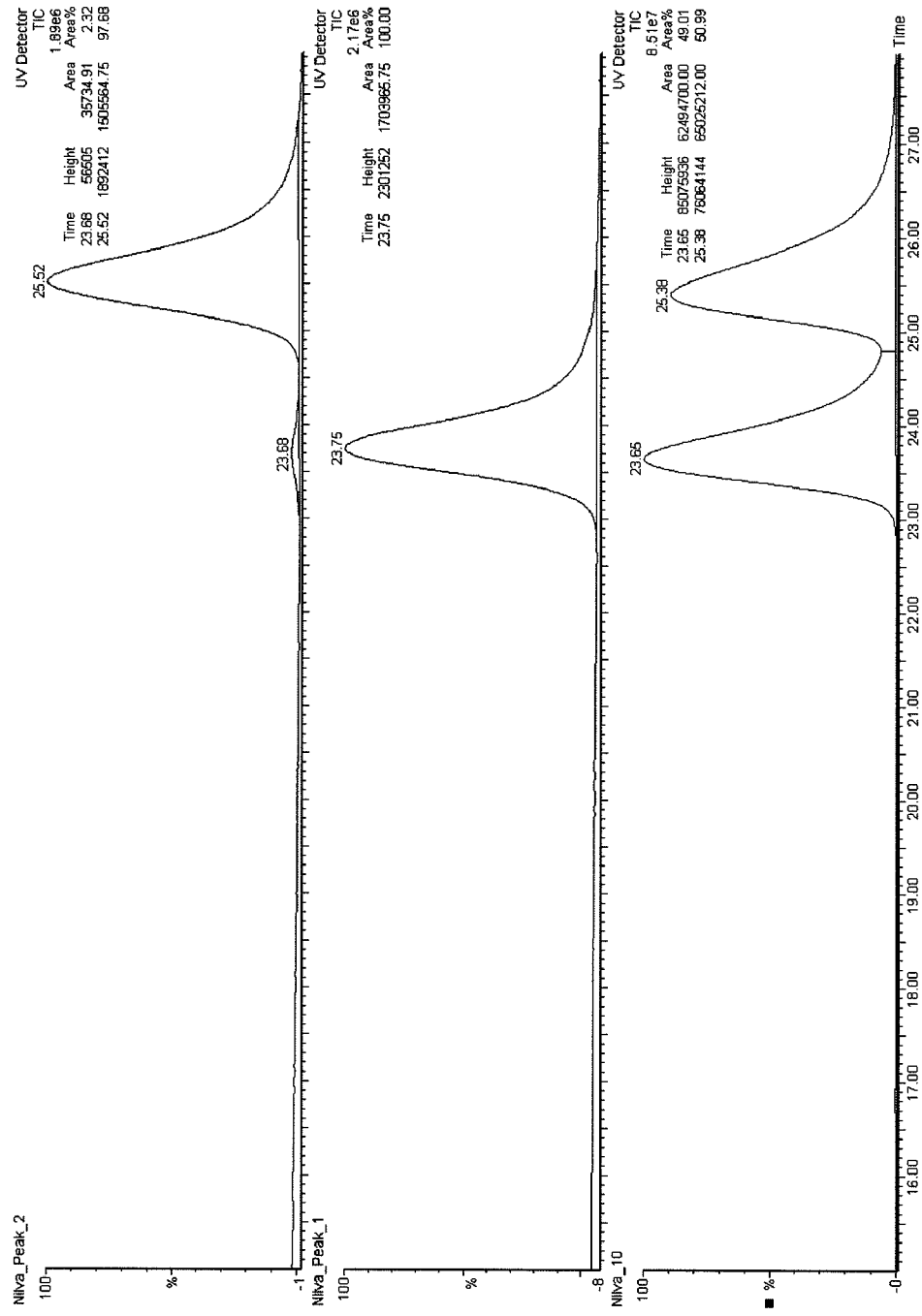
FIG. 8 is a chiral chromatograph showing the separation of the enantiomers of nilvadipine. Nilva_Peak_1 corresponds to (−)-nilvadipine (nilvadipine 1); Nilva_Peak_2 corresponds to (+)-nilvadipine (nilvadipine 2). Nilva_10, which refers to the original racemic mixture of nilvadipine, is included for illustrative purposes.

Examples of methods that can be used to obtain optical isomers of the compounds include the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound, precursor, or semi-synthetic intermediate is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer (see, for example, U.S. Pat. No. 5,508,413 assigned to Fujisawa Pharmaceutical Co., Ltd);

vii) first- and second-order asymmetric transformations a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent; and xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

xiv) liquid chromatography—a technique whereby enantiomers are separated in a normal phase solvent system by virtue of the difference in their partition coefficients with respect to a chiral stationary phase. This technique was employed to generate optically active preparations of (−)-nilvadipine and (+)-nilvadipine described herein (see FIG. 8).

The enantiomers of nilvadipine have been separated as follows:

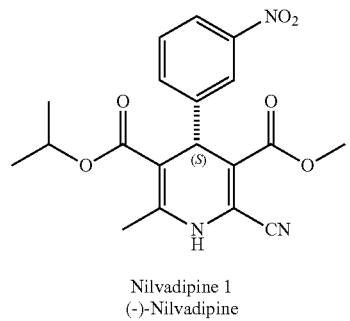

Nilvadipine 1
(−)-Nilvadipine

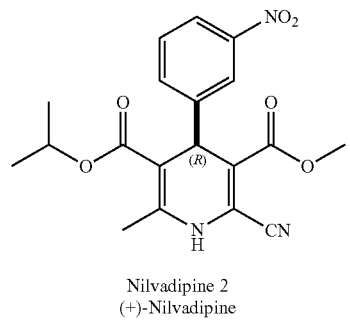

Nilvadipine 2
(+)-Nilvadipine

The literature values for optical rotations of the enantiomers of nilvadipine are reported in Satoh, Y.; Okumura, K.; Shiokawa, Y. *Chem. Pharm. Bull.* 42(4) 950-952 (1994). See FIG. 5 for data regarding the enantiomeric purity of the separated compounds.

By the term "about" is meant within ±10% of the stated amount, or within experimental error of the measuring technique. The phrase "a composition consisting essentially of" is meant to encompass a composition in which the active pharmaceutical ingredient is as indicated. In one embodiment, the phrase "consisting essentially of" excludes non-listed active pharmaceutical ingredients, but does not exclude pharmaceutically acceptable vehicles, carriers, or diluents, or the manner in which the active pharmaceutical ingredient is formulated. In one embodiment, for example in a method of treatment, the phrase "consisting essentially of" may encompass administration of one or more active pharmaceutical ingredients as the sole therapeutic agent(s) for that particular indication, while not excluding therapeutic agents administered for other reasons or indications.

EXAMPLES

The methods of the present invention for reducing the pathological effects of Aβ in animals or humans suffering from diseases associated with amyloidosis, such as AD, will be described in more detail in the following non-limiting examples. Examples 1-5 provide data for racemic nilvadipine for comparative purposes.

Chromatographic Purification of Nilvadipine Enantiomers

Chromatographic purification of both enantiomers of nilvadipine was achieved via High Performance Liquid Chromatography (HPLC) using a stationary phase of modified cellulose (Chiral Technologies, West Chester, Pa.). The chromatographic conditions were as follows: column internal diameter, 10 mm; column length, 250 mm; mobile phase, 95:5 volumetric ratio of hexanes to ethanol; flow rate, 2.5 ml/min; column temperature, 7° C. Repeated injections of racemic nilvadipine using signal-based fraction collection yielded purified enantiomers for the examples described herein. See FIG. 8.

Example 1

Chronic Administration of Nilvadipine on Aβ Deposition (Amyloid Burden)

The effect of chronic administration of nilvadipine on Aβ deposition (amyloid burden) in different regions of the brain of TgAPP$_{sw}$ mice was examined using a 4G8 anti-Aβ monoclonal antibody immunostaining technique. The 4G8 immunostaining technique was chosen for determining the Aβ burden because of its robust signal and optimal results for quantitative analysis of Aβ deposition. Briefly, paraffin sections were subjected to immunohistochemistry as described previously (Nakagawa, Y et al., Exp. Neurol., 163:244-252, 2000). Sections were deparaffinized in xylene, hydrated in a series of ethanol and deionized water, and subjected to an antigen retrieval step by immersing sections in 88% formic acid for 60 min before immunohistochemistry for Aβ. Sections were washed in water, and endogenous peroxidases were quenched using a freshly prepared mixture of methanol (150 ml) plus hydrogen peroxide (33%, 30 ml). The avidin-biotin complex method was used according to the instructions of the vendor (Vector Laboratories, Burlingame, Calif.). Amyloid burden was assessed by determining the percentage of the brain region that stained positive for Aβ. Negative controls included the application of the same immunohistochemistry protocol to sections, except preimmune serum was applied instead of primary antibody. TgAPP$_{sw}$ mice were divided into an experimental group that received an effective amount of nilvadipine (n=7) and a control group that received a vehicle (n=5).

As shown in FIG. 1, treatment with nilvadipine reduced the Aβ burden about 62% in the visual cortex compared to controls, about 65% in the parietal cortex compared to controls, about 58% in the motor cortex compared to controls, about 58% in the pyriform cortex compared to controls, about 52% in the CA1 region of the hippocampus compared to controls, and about 50% in the CA2-CA3 region of the hippocampus compared to controls.

Example 2

Chronic Administration of Nilvadipine on Microglial Activation

The effect of chronic administration of nilvadipine on microglial activation in TgAPP$_{sw}$ mice was examined in three regions of the mouse brain using a CD45 immunostaining technique in which the number of CD45+microglia was determined.

Briefly, immunohistochemistry for CD45, a specific marker of microglia, was conducted on the cryostat brain sections. CD45-positive microglial cells were immunolocalized by incubation with a mouse monoclonal antibody against CD45 (Chemicon International) overnight at 4° C., followed by application of a biotinylated rabbit anti-mouse secondary antibody for 30 minutes. Detection of CD45 was completed with diaminobenzidine chromogen substrate, which produces a brown cell surface stain on CD45-positive microglial cells.

Figure 2:
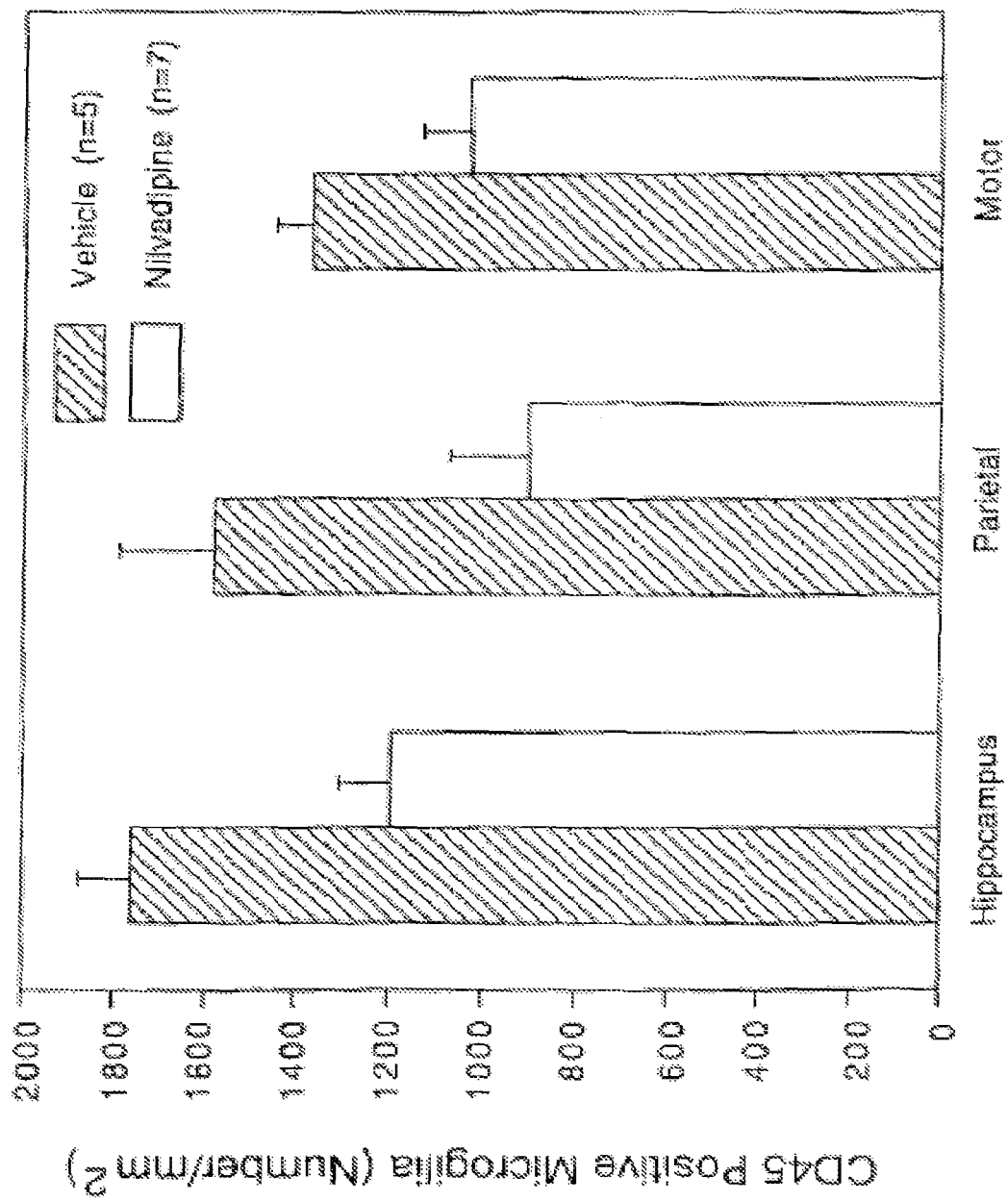
FIG. 2 is a bar graph that illustrates the effect of chronic administration of nilvadipine on microglial activation in TgAPP$_{sw}$ mice in three regions of the brain using a CD45 immunostaining technique that determines the number of CD45+ microglia.

As shown in FIG. 2, nilvadipine treatment administered in an effective dosage amount reduced microglial activation about 33% in the hippocampus, about 43% in the parietal cortex, and about 27% in the motor cortex, when compared to controls.

Example 3

The Effect of Nilvadipine Administration on Microglial Activation

Figure 3:
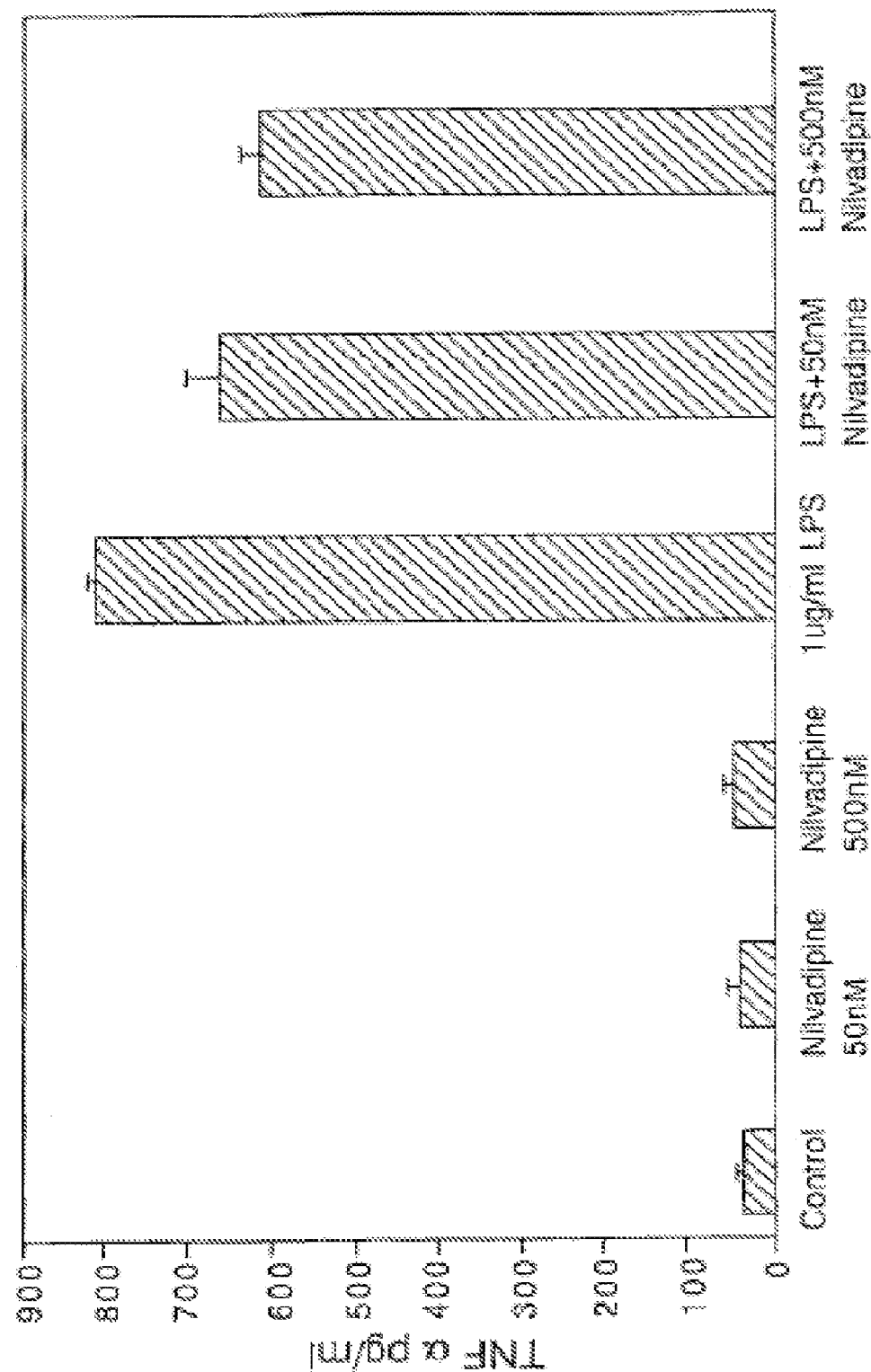
FIG. 3 is a bar graph that illustrates the effect of nilvadipine on microglial activation in N9 murine microglial cells in vitro activated with lipopolysaccharide (LPS) for 24 hours. Microglial activation is determined by TNF-α production (pg/ml) measured by ELISA.

The effect of nilvadipine on microglial activation was examined in N9 murine microglial cells in vitro activated with lipopolysaccharide (LPS) for 24 hours. N9 murine microglial cells are well characterized scavenger murine microglial clones derived from embryonic mouse brain. The extent of microglial activation was determined by TNF-α production (pg/ml) measured by ELISA. As shown in FIG. 3, microglial cells not activated with LPS (control cells) produced about 40 pg/ml TNF-α. Microglial cells in the presence of 50 nM nilvadipine produced about 40 pg/ml TNF-α. Increasing nilvadipine administration 10-fold (500 nM) did not change TNF-α production. Microglial cells in the presence of 1 µg/ml LPS produced about 820 pg/ml TNF-α, an increase of about 95% from the control cells and nilvadipine-administered cells. Microglial cells in the presence of both 1 µg/ml LPS plus 50 nM nilvadipine produced about 670 pg/ml TNF-α. LPS plus 500 nM nilvadipine administration decreased TNF-α production to about 610 pg/ml. Thus, nilvadipine opposed the LPS-induced microglial activation by about 20 to 25%.

Example 4

The Effect of Nilvadipine Administration on Aβ Neurotoxicity

The effect of nilvadipine administration (10 nM and 100 nM) on Aβ neurotoxicity was examined using human neuronal progenitor cells (HNPC) treated for three days with 30 µM of pre-aggregated Aβ1-40 (AgAβ). HNPC cells differentiate into neurons readily upon treatment with cyclic AMP. Cyclic AMP (1 mM) (Sigma) was added to the culture medium and the HNPC cells were incubated at 37° C. for 48 hours or more under serum free conditions. This medium allowed differentiation of the progenitors into cells of neuronal lineage, as was confirmed by the staining of most of the cells with antibodies against the microtubule-associated protein, MAP-2. Neurotoxicity was assessed by measuring the amount of lactic dehydrogenase (LDH; an intracellular enzyme found in all cells) released from the cells.

Figure 4:
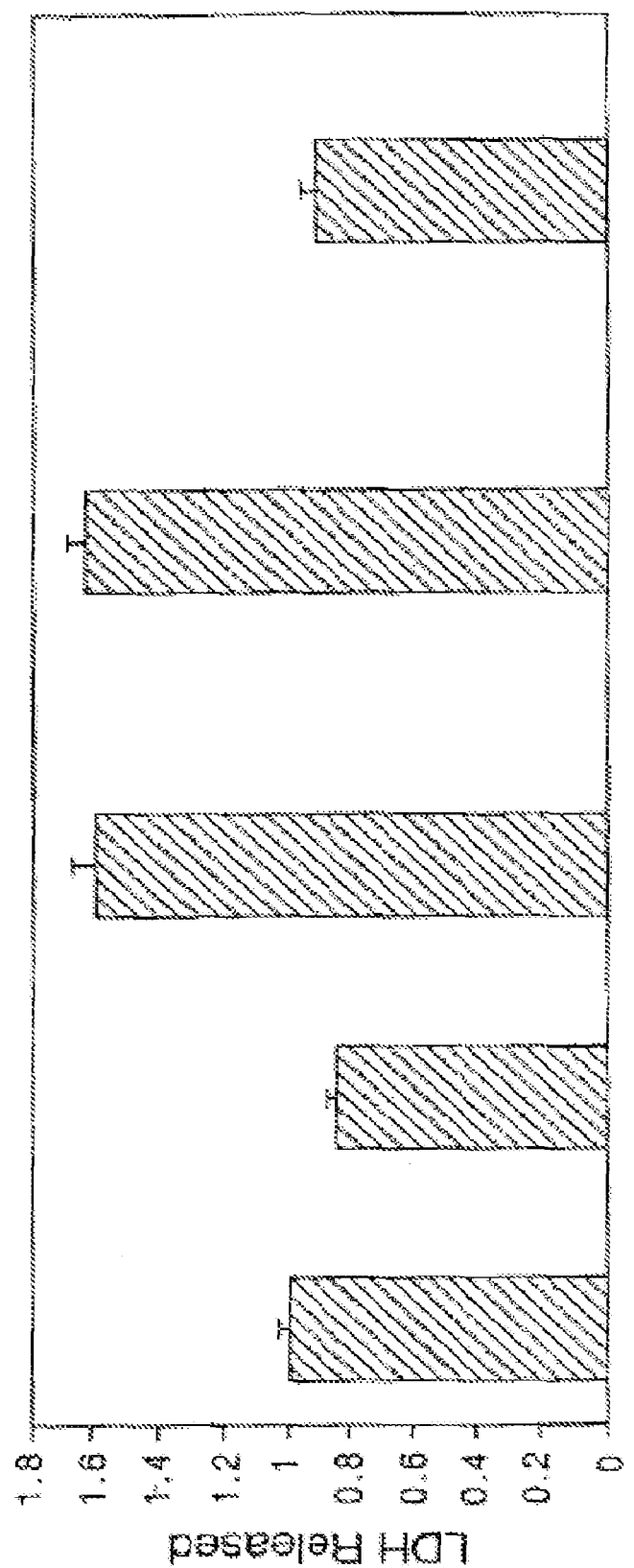
FIG. 4 is a bar graph that illustrates the effect of nilvadipine administration on Aβ neurotoxicity using HPNC cells treated for three days with 30 μM of pre-aggregated Aβ1-40 (AgAβ). Neurotoxicity is assessed by measuring the amount of lactic dehydrogenase (LDH) released from cells.

As shown in FIG. 4, treatment of the cells with AgAβ produced about a 44% increase in LDH release compared to treatment of the cells with nilvadipine. There was no change in LDH release when 10 nM nilvadipine was added along with AgAβ. However, when the dosage amount of nilvadipine was increased 10-fold to 100 nM, the amount of LDH release was decreased by about 44%.

Example 5

The Effect of Nilvadipine Administration on APP Processing

The effect of nilvadipine on APP processing was examined using human glioblastoma cells transfected with APP$_{sw}$. The cells were treated with 50 nM and 250 nM nilvadipine for 24 and 48 hours, and production of Aβ1-40 in the culture medium was measured by using a commercially available human Aβ1-40 ELISA (Biosource, CA).

Figure 5A:
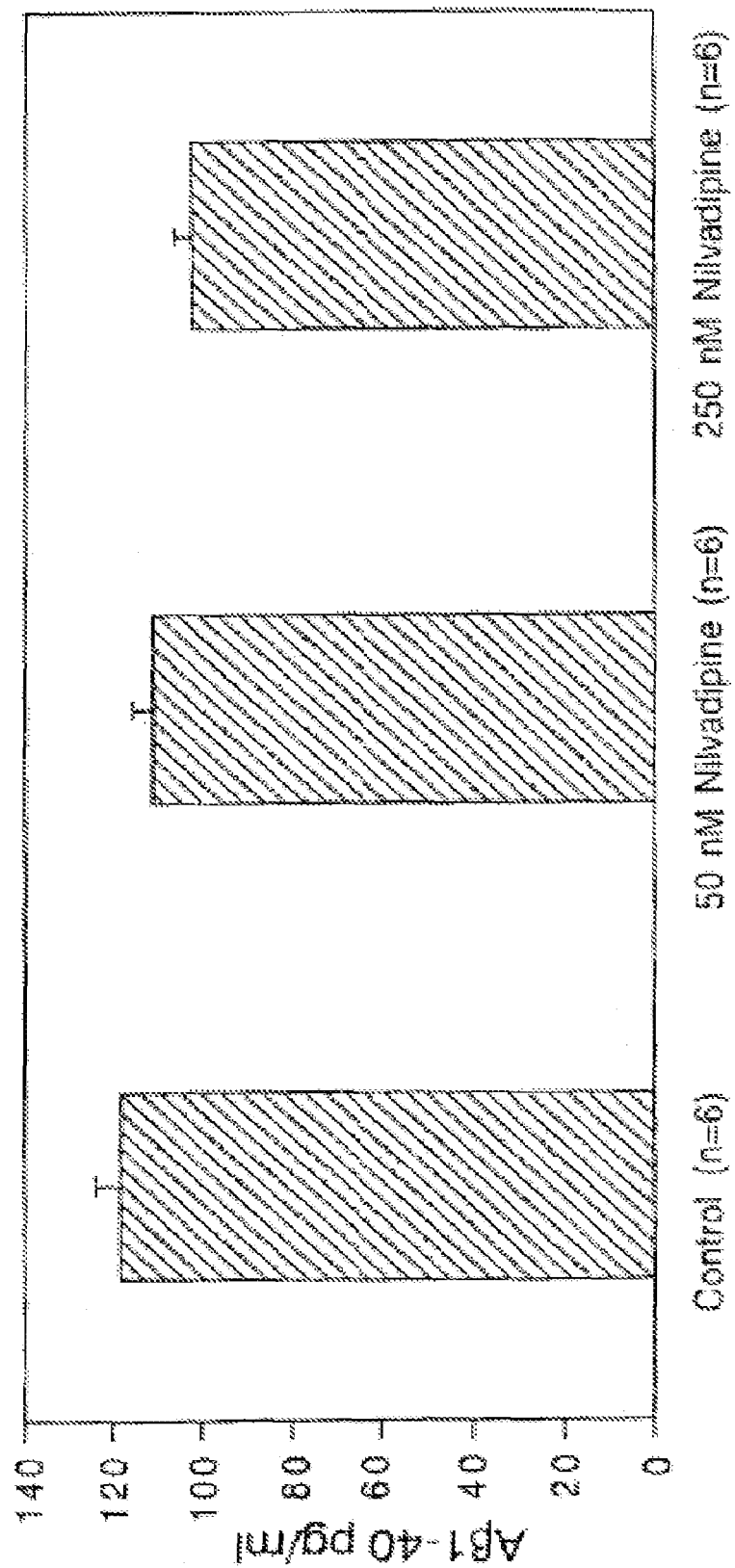
FIGS. 5A and 5B are bar graphs that illustrate the effect of nilvadipine on APP processing using human glioblastoma cells transfected with $APP_{sw}$. Cells were treated with 50 nM and 250 nM nilvadipine for 24 hours (FIG. 5A) and for 48 hours (FIG. 5B). Production of Aβ1-40 in the culture medium was measured by ELISA.
Figure 5B:
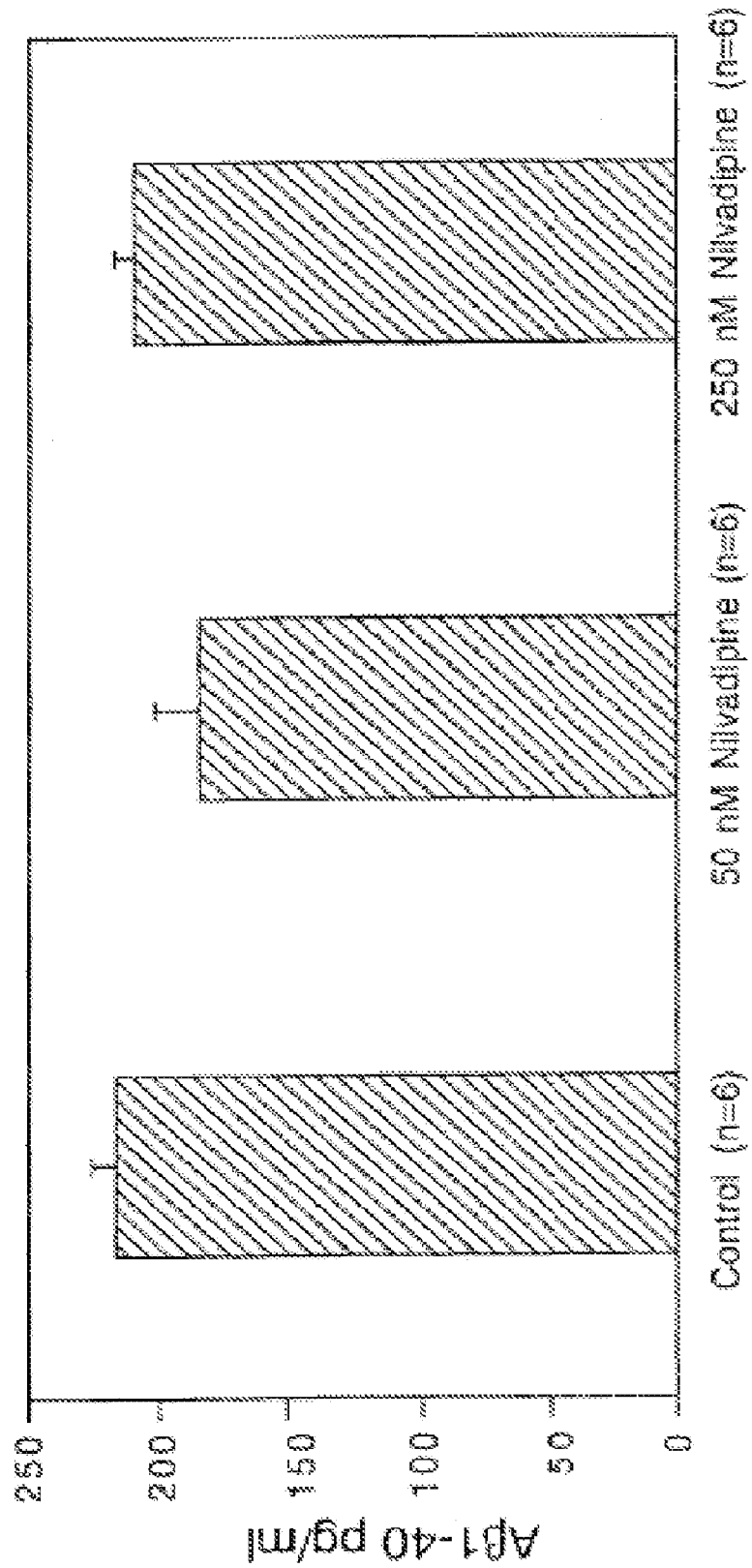

As shown in FIG. 5A, after 24 hours of treatment, 50 nM of nilvadipine reduced the production of Aβ1-40 by about 9%, and 250 nM of nilvadipine reduced Aβ1-40 production by about 15%. After 48 hours of treatment (FIG. 5B), 50 nM of nilvadipine reduced the production of Aβ1-40 by about 18%, and 250 nM of nilvadipine reduced Aβ1-40 production by about 5%.

Example 6

The Effect of Varying Doses of Racemic and Isolated Enantiomers of Nilvadipine on Aβ Levels The effect of pure enantiomeric forms of nilvadipine, (−)-nilvadipine (nilvadipine 1) and (+)-nilvadipine (nilvadipine 2) (FIG. 8) as well as a mixture of the two enantiomers (in equal proportion) on Aβ1-40 and Aβ1-42 production was examined using 7W WT APP751 Chinese hamster ovary cells following 24 hours treatment. Production of Aβ1-40 and Aβ1-42 in the culture medium was measured by using a commercially available human Aβ1-40 ELISA (Biosource, CA) and commercially available human Aβ1-42 ELISA (Biosource, CA), respectively.

Figure 6:
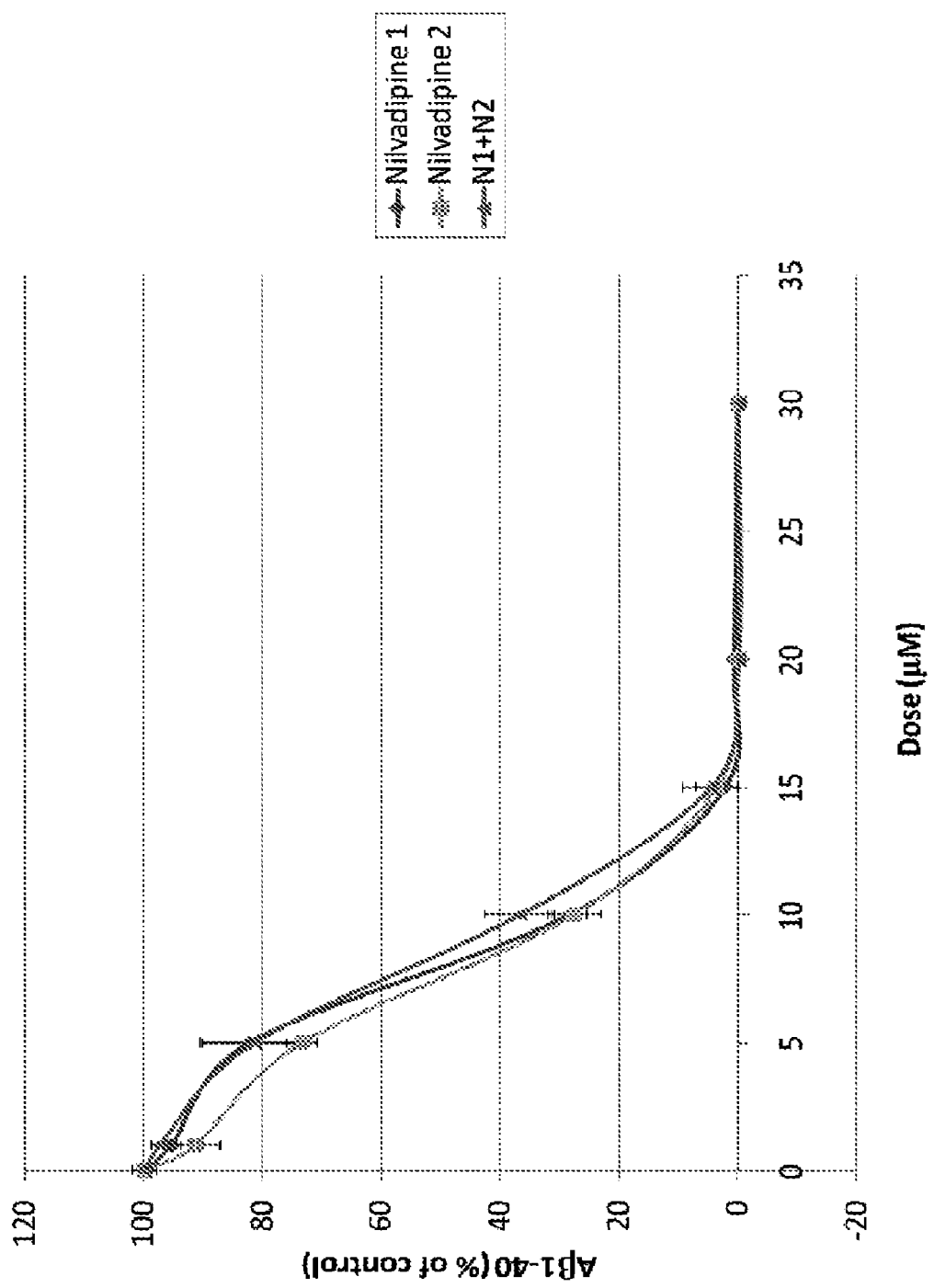
FIG. 6 is a dose response curve showing the effect of pure enantiomeric forms of nilvadipine (nilvadipine 1 and nilvadipine 2) as well as a mixture of the 2 enantiomers in equal proportion (N1+N2) on Aβ1-40 production by 7W WT APP751 Chinese hamster ovary cells following 24 hours treatment. Both enantiomers appear to dose dependently inhibit Aβ1-40 production in a similar fashion.
Figure 7:
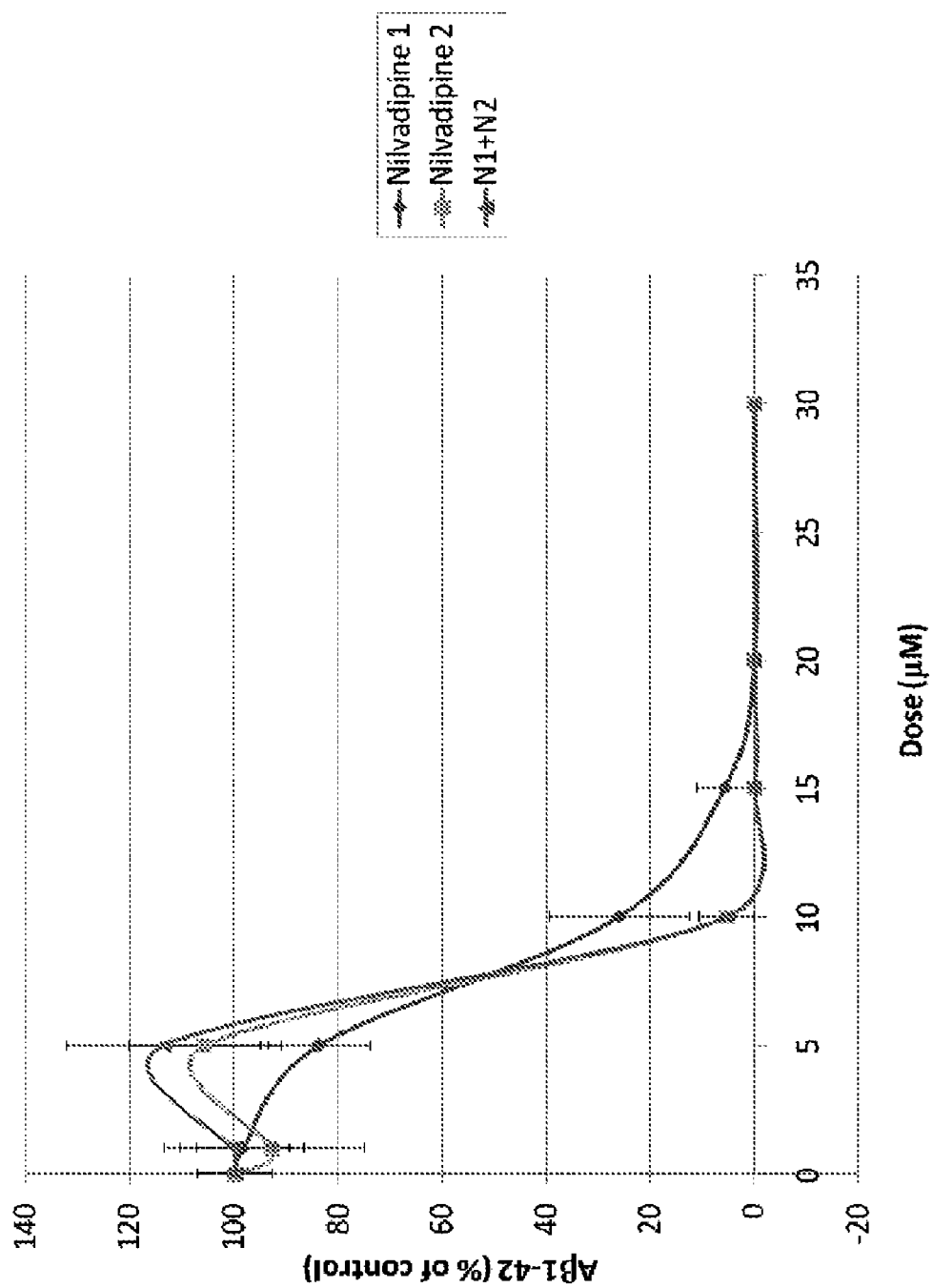
FIG. 7 is a dose response curve showing the effect of pure enantiomeric forms of nilvadipine (nilvadipine 1 and nilvadipine 2) as well as a mixture of the 2 enantiomers in equal proportion (N1+N2) on Aβ1-42 production by 7W WT APP751 Chinese hamster ovary cells following 24 hours treatment. Note that the pure enantiomer nilvadipine 2 as well as the racemic mixture of nilvadipine (N1+N2) slightly stimulate Aβ1-42 at low dose whereas the enantiomer nilvadipine 1 is deprived of such effect.

As shown in FIG. 6, both enantiomers appear to dose dependently inhibit Aβ1-40 production in a similar fashion. However, the (+)-nilvadipine (nilvadipine 2) as well as the racemic mixture of nilvadipine (N1+N2) slightly stimulate Aβ1-42 at low dose whereas (−)-nilvadipine (nilvadipine 1) does not show this effect (FIG. 7).

Example 7

Effect of Isolated Enantiomers of Nilvadipine on Vasoconstriction in Rat Aortae

The effect of pure enantiomeric forms of nilvadipine, (−)-nilvadipine (nilvadipine 1) and (+)-nilvadipine (nilvadipine 2) (FIG. 8) on FPL64176 induced vasoconstriction in rat aortae was examined. Normal male Sprague-Dawley rats (7-8 months old) were humanely euthanatized, and freshly dissected rat aortae were segmented into 3-mm rings and suspended in Kreb's buffer on hooks in a vessel bath apparatus. These hooks were connected to an isometric transducer linked to a MacLab system. Aortic rings were equilibrated in the tissue bath system for 2 h with the Kreb's buffer changed every 30 min. A baseline tension of 2 g was applied to each aortic ring. Aortic rings were pretreated with 100 nM of (−)-nilvadipine (nilvadipine 1), 100 nM of (+)-nilvadipine (nilvadipine 2) or untreated 2 min prior to the addition of 1 μM of FPL64176 (2,5-dimethyl-4[2-(phenylmethyl)benzoyl]-1H-pyrrole-3-carboxylic acid methyl ester), a potent and selective agonist of L-type calcium channels. Aortic rings were constricted with FPL64176 for 30 minutes. The amount of contraction (in g) as compared to baseline was determined and the means and standard deviation of all such values were calculated.

Figure 9:
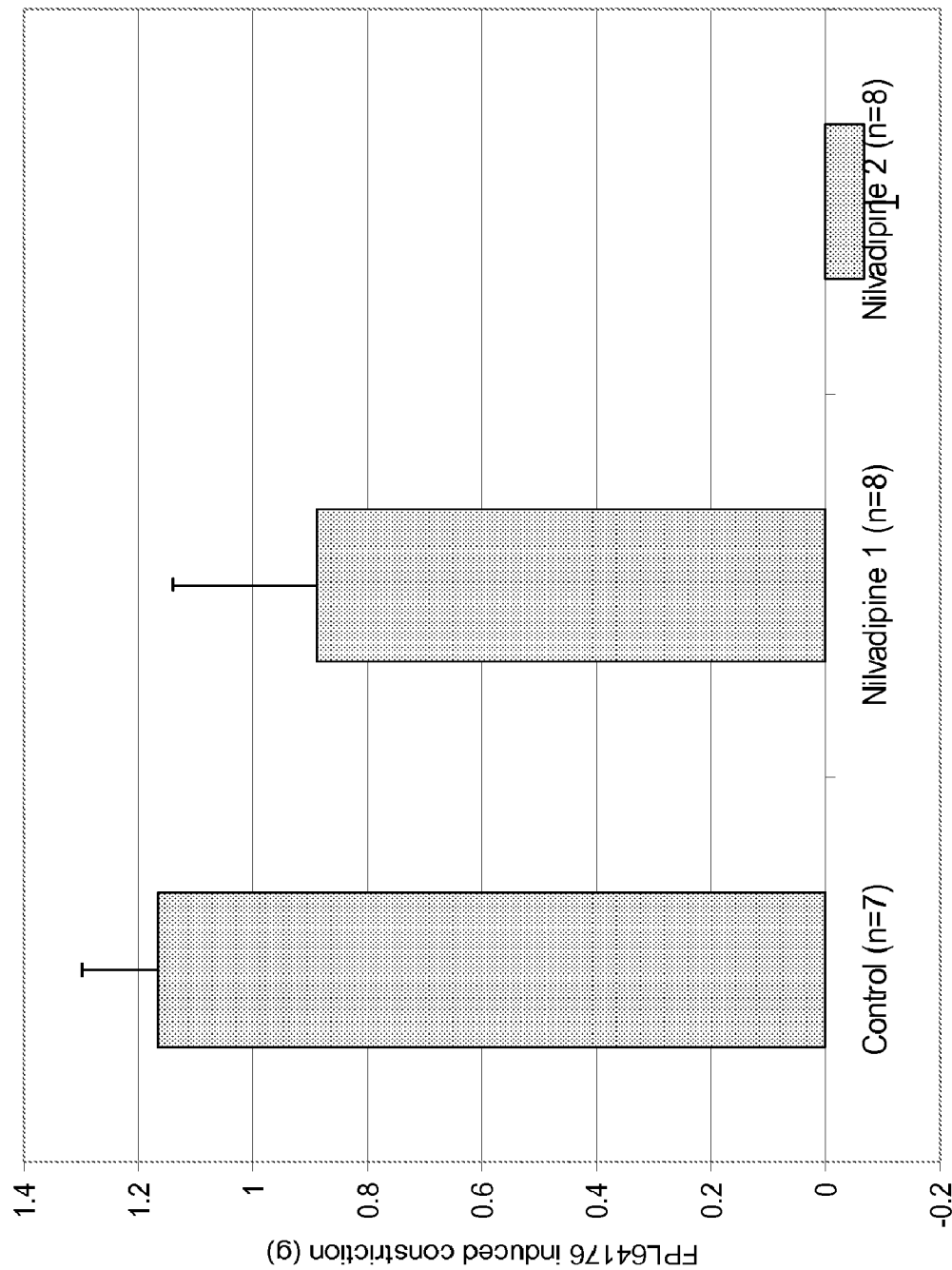
FIG. 9 shows the effect of (−)-nilvadipine (nilvadipine 1) and (+)-nilvadipine (nilvadipine 2) on FPL64176 induced vasoconstriction in rat aortae. Data show that (+)-nilvadipine completely antagonizes FPL64176 induced vasoconstriction whereas (−)-nilvadipine does not affect the vasoactive effect of the L-type calcium channel agonist showing that (+)-nilvadipine is a L-type calcium channel blocker whereas (−)-nilvadipine is deprived of such effect.

As shown in FIG. 9, (+)-nilvadipine completely antagonizes FPL64176 induced vasoconstriction whereas (−)-nilvadipine does not produce the vasoactive effect of the L-type calcium channel agonist showing that (+)-nilvadipine is an L-type calcium channel blocker whereas (−)-nilvadipine is deprived of such effect. The data presented herein demonstrates baseline aortic contraction when challenged with FPL64176 for the (−)-enantiomer, which correlates with reduced vasoactivity for the (−)-enantiomer compared to the racemic mixture or (+)-enantiomer which exhibit vasoactivity (i.e., antagonism of induced vasoconstriction).

Example 8

The Effect of (−)-Nilvadipine on Brain Aβ Levels

The effect of isolated (−)-nilvadipine on brain Aβ1-40 and Aβ1-42 levels was examined. 93-weeks old male transgenic APP$_{sw}$ mice (Tg APP$_{sw}$ line 2576) were injected intraperitoneally daily with 10 mg/Kg of body weight of (−)-nilvadipine dissolved in DMSO (n=4) or with the same volume (n=4) of vehicle (100 μL). Following 4 days of treatment, animals were humanely euthanatized one hour after the last injection, their brains collected and snapped frozen in liquid nitrogen. Brains were homogenized at 4° C. in distilled water containing 1× of the protease inhibitors cocktail IV (Calbiochem, CA) and centrifuged at 14,000 rpm for 30 min at 4° C. The pellet was resuspended with an equal volume of Guanidine 5M dissolved in Tris HCl Buffer (pH=8) and incubated at room temperature for one hour. Protein concentrations were determined in the guanidine treated samples with the BCA method (Biorad, CA). Aβ1-40 and Aβ1-42 levels were evaluated by ELISA (Biosource, CA) and results were reported in pg of Aβ1-40 or Aβ1-42 per mg of protein.

Figure 10:
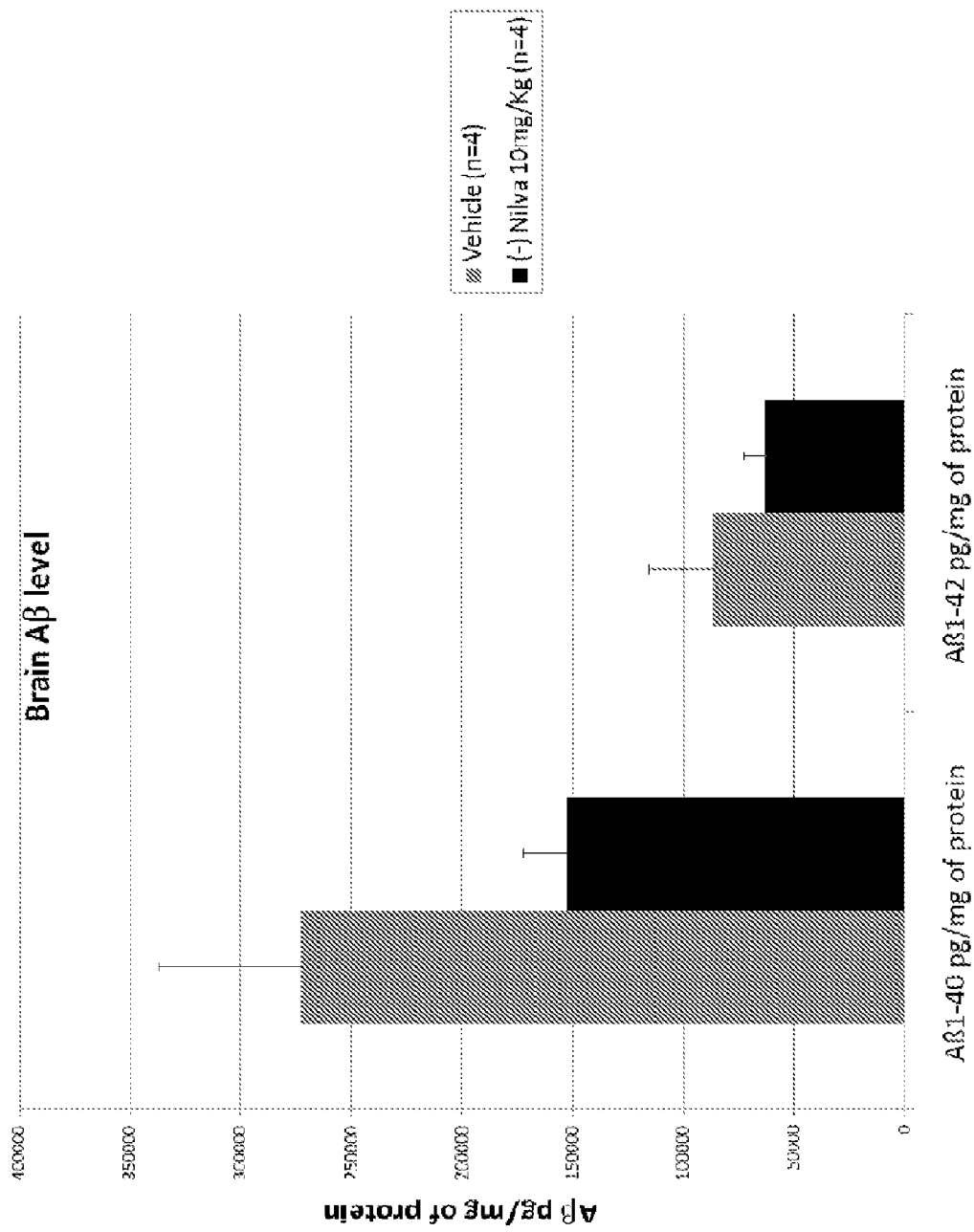
FIG. 10 is a bar graph that illustrates the effect of (−)-nilvadipine on brain Aβ1-40 and Aβ1-42 levels in 93-week old Tg $APP_{sw}$ mice. Animals were treated intraperitoneally daily for four days with (−)-nilvadipine (10 mg/kg of body weight).

As shown in FIG. 10, administration of (−)-nilvadipine to TgAPP$_{sw}$ mice at a dose of 10 mg/kg body weight daily for four days resulted in a 26% decrease in the brain levels of Aβ1-42 (pg/ml), and a 43% decrease in the brain levels of Aβ1-40, compared to the control animals.

Example 9

The Effect of a Slow Release (−)-Nilvadipine on Brain Aβ Levels

The effect of a slow release of (−)-nilvadipine on brain Aβ1-42 levels was examined. 66 week-old Tg APP$_{sw}$ (Tg APP$_{sw}$ line 2576) were implanted subcutaneously with a biodegradable pellet of (−)-nilvadipine ensuring a continuous slow release of 30 mg of (−)-nilvadipine/Kg of body weight/day (n=5), a biodegradable pellet of (−)-nilvadipine ensuring a release of 56 mg/Kg/Day (n=6), or a pellet releasing a placebo (n=6) for a period of 30 days. Animals were humanely euthanatized 26 days after the pellet implantation, their brains collected and snapped frozen in liquid nitrogen. Brains were homogenized at 4° C. in distilled water containing 1× of the protease inhibitors cocktail IV (Calbiochem, CA) and centrifuged at 14,000 rpm for 30 min at 4° C. The supernatant was resuspended with an equal volume of Guanidine 5M dissolved in Tris HCl Buffer (pH=8) and incubated at room temperature for one hour. Protein concentrations were determined in the guanidine treated samples with the BCA method (Biorad, CA). Aβ1-42 levels were evaluated by ELISA (Biosource, CA) and results were reported in pg of Aβ1-42 per mg of protein.

Figure 11:
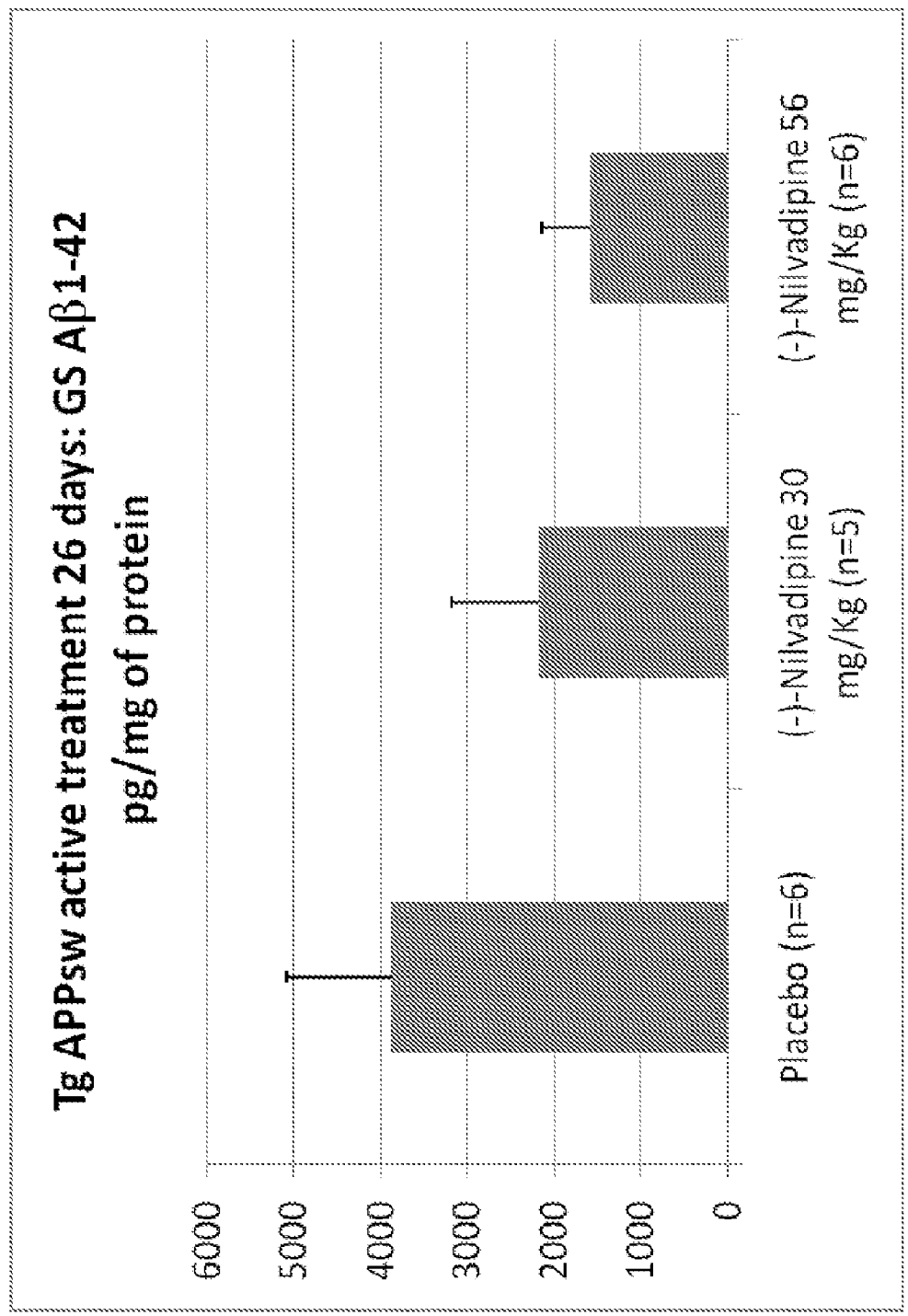
FIG. 11 is a bar graph that illustrates the effect of a slow release of (−)-nilvadipine on brain Aβ1-42 levels in 70-week old Tg $APP_{sw}$ mice Animals were treated for 26 days using biodegradable pellets that were implanted subcutaneously.

As shown in FIG. 11, administration of slow release (−)-nilvadipine to TgAPP$_{sw}$ mice resulted in a 2 fold reduction in the level of brain Aβ1-42 for the mice dosed with a 30 mg/Kg/Day slow released pellet of (−)-nilvadipine whereas a 2.5 fold reduction in Aβ1-42 was observed in the animals treated with a 56 mg/Kg/Day slow released pellet compared to mice implanted with a placebo pellet.

Example 10

Figure 12:
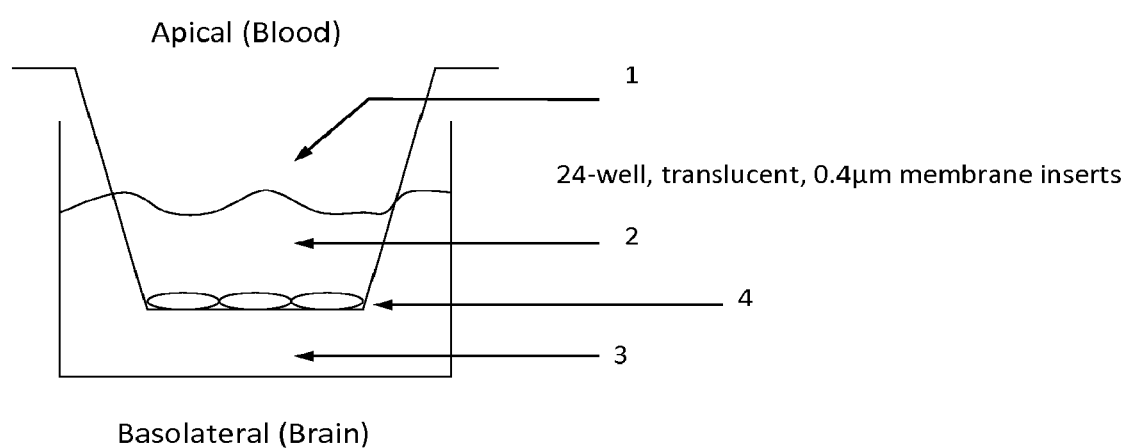
FIG. 12 illustrates an in vitro model of the Blood Brain Barrier using 24-well, translucent, 0.4 μm membrane inserts containing a layer of Human Brain Microvascular Endothelial Cells (HBMEC). The migration of fluorescein-beta amyloid 1-42 into the apical compartment was assessed at various time points.

The Effect of (−)-Nilvadipine on the Clearance of Brain Aβ Levels Across the Blood Brain Barrier In Vitro Model The effect of (−)-nilvadipine on the clearance of brain Aβ levels across the Blood Brain Barrier (BBB) was examined using both an in vitro and an in vivo model. The in vitro model is shown in FIG. 12. Endothelial cell culture medium (ECM, ScienCell Research Laboratories) containing 2 μM fluorescein-β-amyloid (1-42) (3) was placed in the basolateral (donor) compartment. The apical (receiver) side of the membrane was exposed to various dihydropyridine (DHP) compounds (1, 5, and 10 μM) in ECM (2). The donor compartment was sampled at time 0 to establish the initial concentration of fluorescein-β-amyloid (1-42) in each group. Following exposure of the insert to the well containing fluorescent amyloid, samples were collected from the apical compartment at various time points up to 90 minutes (1) to assess the movement of fluorescein-β-amyloid (1-42) across the human brain microvascular endothelial cell (HBMEC) monolayer (4) (basolateral to apical). The samples were analyzed (λex=485 nm and λem=516 nm) for fluorescein-β-amyloid (1-42) using a BioTek Synergy HT multi-detection microplate reader (Winooski, Vt.). The apparent permeability (Papp) fluorescein-β-amyloid (1-42) was determined using the equation Papp=1/AC$_0$*(dQ/dt), where A represents the surface area of the membrane, C$_0$ is the initial concentration of fluorescein-β-amyloid (1-42) in the basolateral donor compartment, and dQ/dt is the amount of fluorescein-β-amyloid (1-42) appearing in the apical receiver compartment in the given time period (polli). The Papp of fluorescein-β-amyloid (1-42) in the presence of (−)-nilvadipine was compared to control wells and expressed as a percentage.

Figure 13:
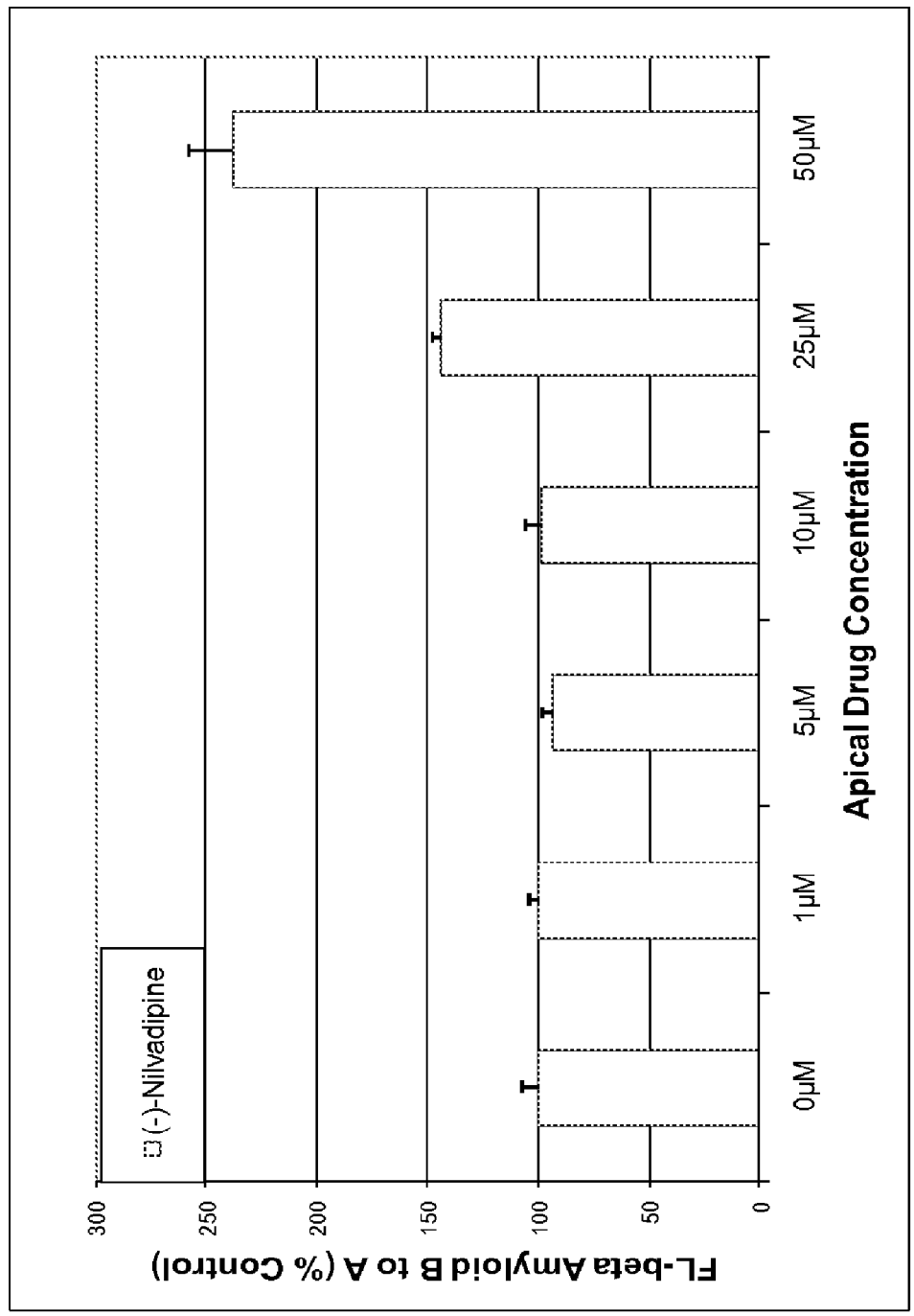
FIG. 13 is a bar graph showing the in vitro effect of (−)-nilvadipine on the clearance of brain Aβ across the Blood Brain Barrier. A=Apical, B=Basolateral.

As shown in FIG. 13, (−)-nilvadipine dose dependently stimulates the transport of Aβ from the brain side (B) to the peripheral side (A) in an in vitro model of the blood brain barrier.

Figure 14:
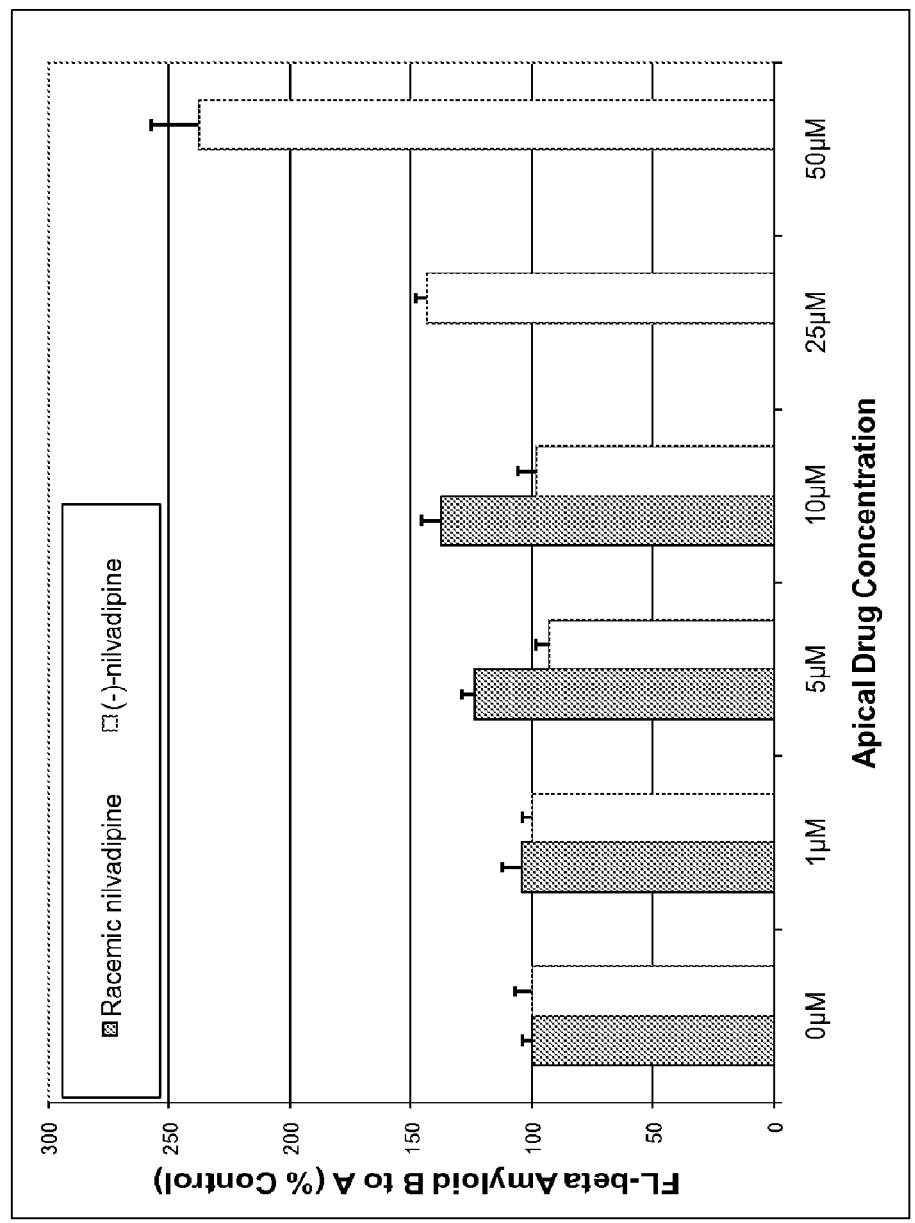
FIG. 14 is a bar graph showing the in vitro effect of (−)-nilvadipine vs nilvadipine racemic mixture on the clearance of brain Aβ across the Blood Brain Barrier. A=Apical, B=Basolateral.

The in vitro model was also used to examine the in vitro effect of (−)-nilvadipine vs nilvadipine racemic mixture on the clearance of brain Aβ across the BBB. A similar protocol to the one described above was used in these experiments, with the primary difference being the addition of a racemic mixture for comparison. As shown in FIG. 14, both (−)-nilvadipine and nilvadipine racemic mixture dose dependently stimulate the transport of Aβ across the blood brain barrier from the brain (B) to the periphery (A) in an in vitro model.

In Vivo Model

The effect of (−)-nilvadipine on the clearance of brain Aβ levels across the BBB was examined using an in vivo model. Wild-type female B6/SJL mice were anesthetized via inhalation using a 3% isoflurane/oxygen mixture. While under anesthesia, the mice were injected with vehicle (DMSO) or (−)-nilvadipine intraperitoneally (i.p.). Five minutes after the i.p. injection, the mice were stereotaxically injected with 3 µl of human β-amyloid (1-42) (1 mM in DMSO) in the intraventricular region of the brain (3 mm posterior and 1.0 mm lateral to the bregma and 4 mm below the surface of the brain). Ten minutes after the injection of human β-amyloid (1-42), the mice were euthanized. Plasma samples were collected and analyzed for human β-amyloid (1-42) using a sandwich ELISA for human β-amyloid (1-42). The level of β-amyloid (1-42) in the plasma samples collected from the (−)nilvadipine treated mice was compared to those receiving vehicle alone. Additionally, similar experiments were performed using animals implanted subcutaneously with a biodegradable pellet of (−)-nilvadipine or a placebo and receiving the intracerebral injection of Aβ1-42 13 days after the pellet implantation. All experiments using animals were performed under protocols approved by the Institutional Animal Care and Use Committee.

Figure 15:
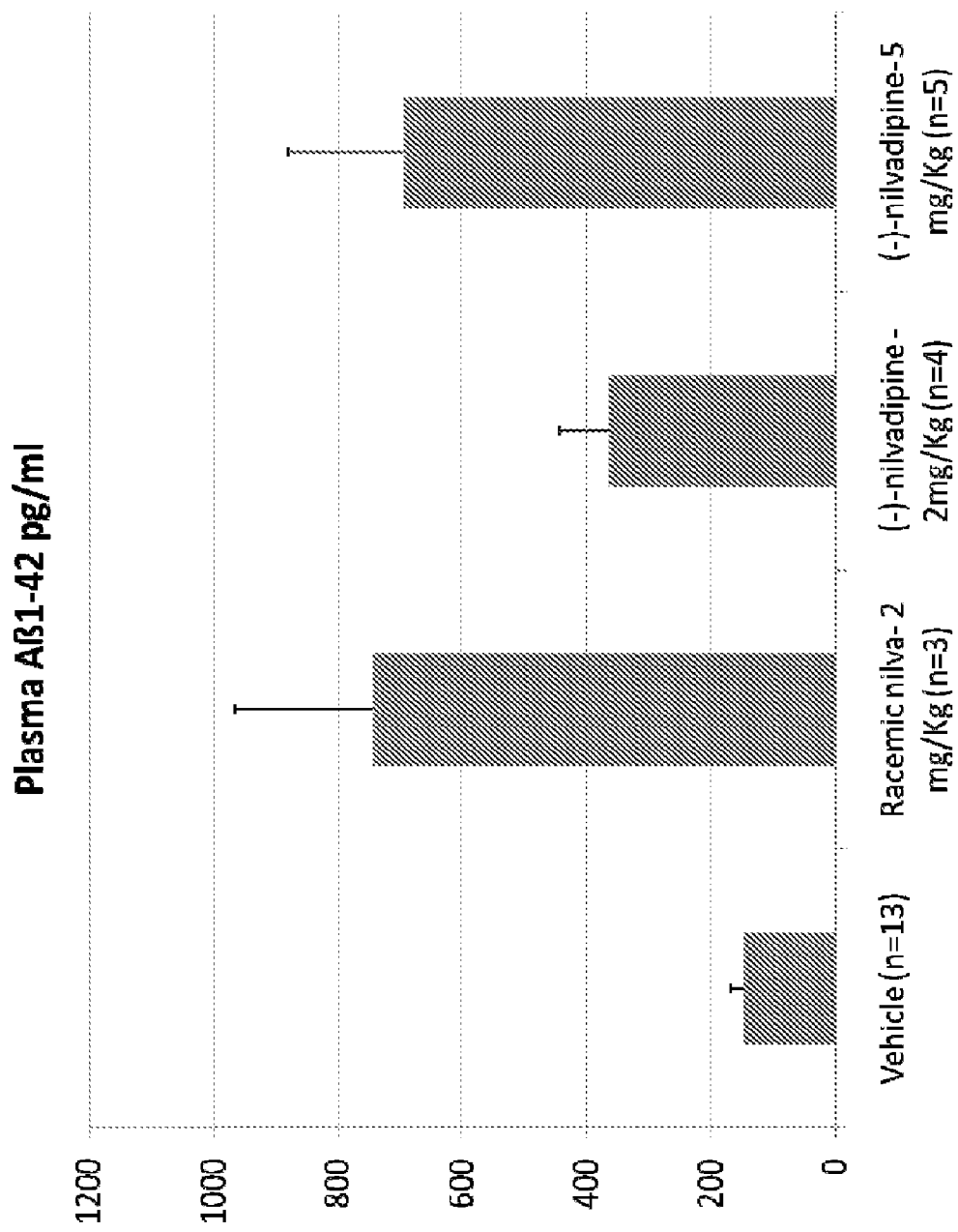
FIG. 15 is a bar graph showing the in vivo effect of (−)-nilvadipine on the clearance of brain Aβ across the Blood Brain Barrier, as measured by plasma Aβ levels in mice.

As shown in FIG. 15, both nilvadipine racemic mixture and (−)-nilvadipine increase the transport of Aβ across the blood brain barrier in vivo. (−)-nilvadipine at 2 mg/Kg of body weight stimulates the clearance of Aβ from the brain to the blood by 2 fold and by 4 fold at a dosage of 5 mg/Kg of body weight whereas nilvadipine racemic mixture increases the clearance of Aβ by 4 fold at a dosage of 2 mg/Kg of body weight.

Figure 16:
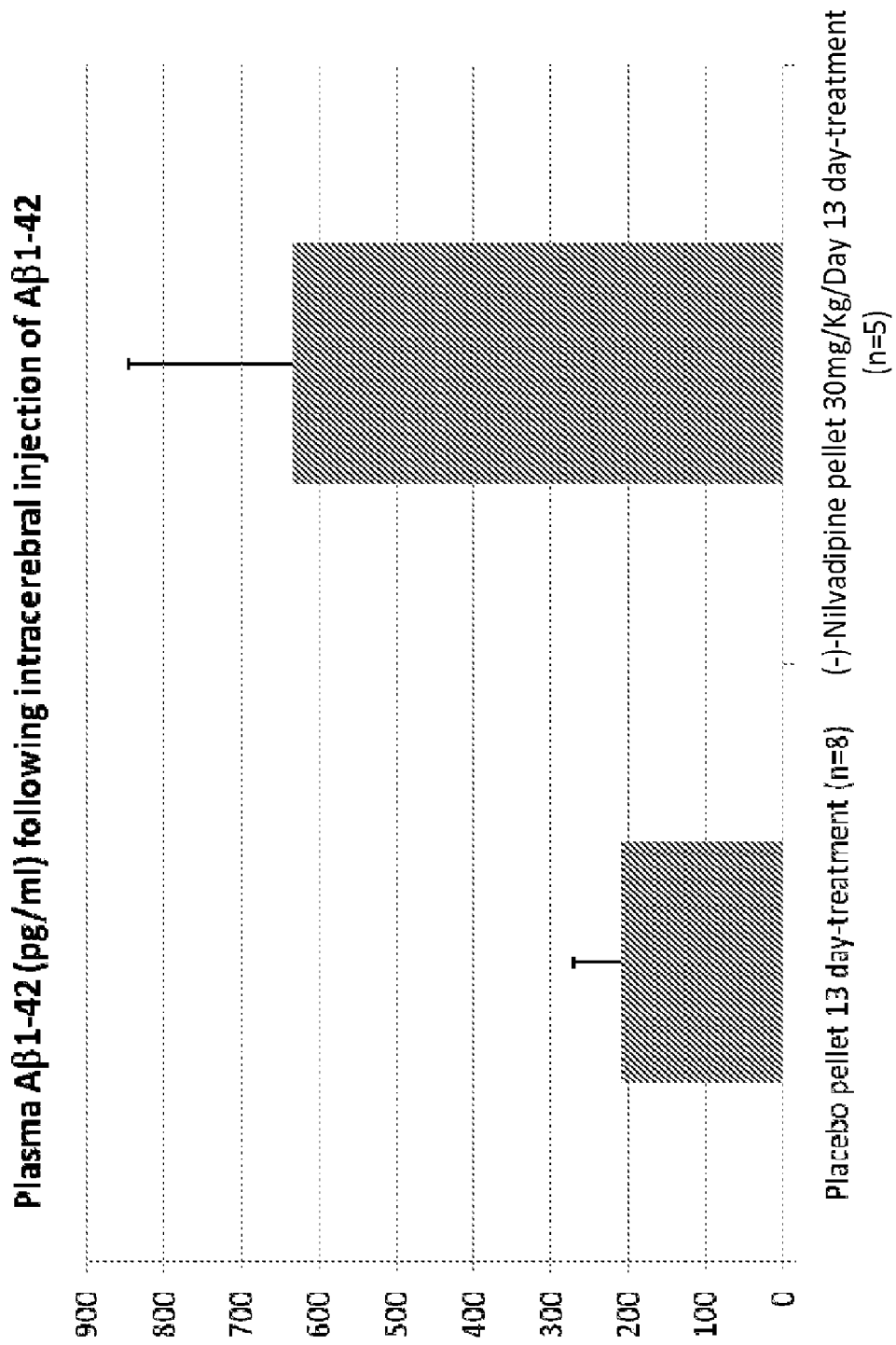
FIG. 16 is a bar graph showing the in vivo effect of a biodegradable (−)-nilvadipine pellet on the clearance of brain Aβ across the Blood Brain Barrier.

FIG. 16 is a bar graph illustrating the effect of (−)-nilvadipine on the clearance of brain Aβ levels across the BBB using animals implanted subcutaneously with a biodegradable pellet of (−)-nilvadipine or a placebo and receiving an intracerebral injection of Aβ1-42 13 days after the pellet implantation. As shown in FIG. 16, a slow release of (−)-nilvadipine ensured by a biodegradable pellet at a dosage of 30 mg/Kg of body weight/Day increases the clearance of intracerebral Aβ by 3 fold compared to controlled mice implanted with a placebo pellet.

These in vitro and in vivo studies of the effect of (−)-nilvadipine on the clearance of brain Aβ levels across the Blood Brain Barrier (BBB) reveal a potentially therapeutically-relevant result. The data suggests that (−)-nilvadipine's effect on clearance is to increase the migration of brain Aβ across the BBB. This stems from the observed increase in serum Aβ levels after administration of (−)-nilvadipine.

Figures 17A, 17B:
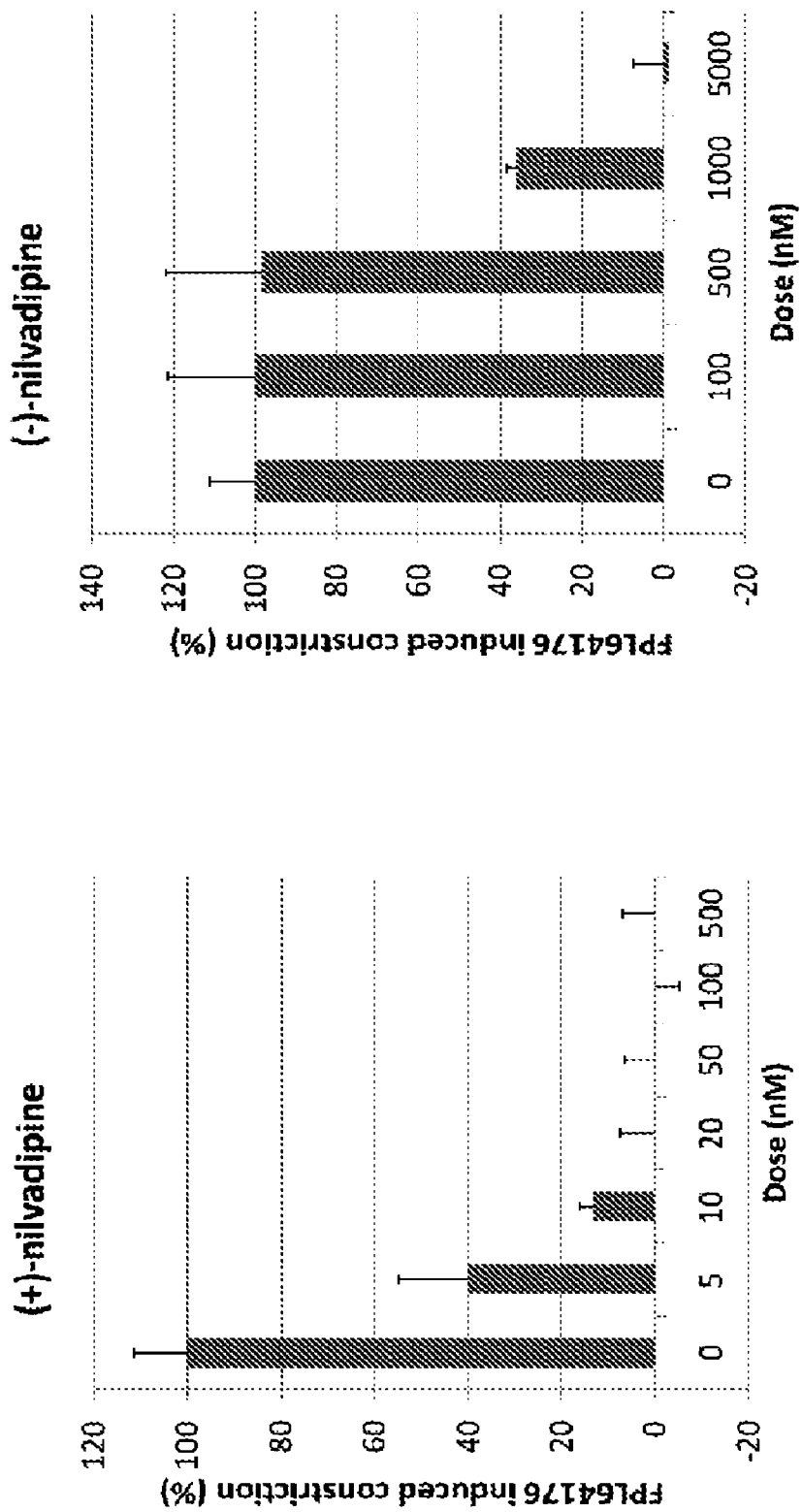
FIGS. 17A and 17B show the vasoactive properties of (+)-nilvadipine versus (−)-nilvadipine over a range of drug dosages.

As shown in FIGS. 17A and B, (−)-nilvadipine can be administered at a much higher dose in the FPL64176 rat aorta model of vasoconstriction before exhibiting vasoactive properties compared to (+)-nilvadipine.

GENERAL CONCLUSIONS

Regarding the effects of the different enantiomers of nilvadipine, both enantiomers appear to dose dependently inhibit Aβ1-40 production in a similar fashion, although (+)-nilvadipine and racemic nilvadipine slightly stimulate Aβ1-42 at low dose. (−)-Nilvadipine's effect on Aβ1-42 is lower and not statistically significant. See, for example, FIGS. 6 and 7. It was also surprisingly discovered that (+)-nilvadipine completely antagonizes FPL64176-induced vasoconstriction whereas (−)-nilvadipine does not antagonize the FPL64176-induced vasoconstriction of the L-type calcium channel agonist. The data presented herein demonstrates baseline aortic contraction when challenged with FPL64176 for the (−)-enantiomer, which correlates with reduced vasoactivity for the (−)-enantiomer compared to the racemic mixture or (+)-enantiomer which exhibit vasoactivity (i.e., antagonism of induced vasoconstriction). An assessment of the influence of (−)-nilvadipine on brain Aβ levels shows that administration of (−)-nilvadipine (10 mg/kg body weight daily) produces a 26% decrease in the brain levels of Aβ1-42 (pg/ml), and a 43% decrease in the brain levels of Aβ1-40, in TgAPP$_{sw}$ mice after only four days of treatment. As shown in FIG. 11, administration of slow release (−)-nilvadipine to TgAPP$_{sw}$ mice over 26 days resulted in a 2 fold reduction in the level of brain Aβ1-42 for the mice dosed with a 30 mg/Kg/Day slow released pellet of (−)-nilvadipine whereas a 2.5 fold reduction in Aβ1-42 was observed in the animals treated with a 56 mg/Kg/Day slow released pellet compared to mice implanted with a placebo pellet.

The in vitro and in vivo studies of the effect of (−)-nilvadipine on the clearance of brain Aβ levels across the Blood Brain Barrier (BBB) also produce unexpected and encouraging results. The data suggests that (−)-nilvadipine's effect on this clearance is to increase the migration of brain Aβ across the BBB. This stems from the observed increase in serum Aβ levels after administration of (−)-nilvadipine.

In view of the above data, it can be extrapolated that enantiomerically-enriched (−)-nilvadipine administration to animals or humans afflicted with a cerebral amyloidogenic disease, such as AD, can significantly decrease the amount of Aβ deposition in critical regions of the brain that characteristically demonstrate an abundance of such pathological deposits as well as reduce the amount of Aβ already deposited in the brain without unnecessarily affecting blood pressure or other possible side effects. Additionally, enantiomerically-enriched (−)-nilvadipine administration may oppose the neurotoxic effects of Aβ, effects which are believed to be responsible for the widespread and devastating neuronal destruction seen with AD, as well as reduce microglial activation that causes the characteristic inflammatory response seen in the brains of AD patients with reduced side effects. Finally, enantiomerically-enriched (−)-nilvadipine treatment may reduce the concentration of already deposited Aβ in brains of animals or humans afflicted with cerebral amyloidogenic diseases such as AD without causing unwanted side effects.

It will be apparent to those skilled in the art that various modifications and variations can be made in the methods of the present invention without departing from the spirit or scope of the invention. Thus, it is intended that the present invention include modifications and variations that are within the scope of the appended claims and their equivalents. All references cited herein are incorporated by reference.

The invention claimed is:

1. A pharmaceutical composition comprising optically active nilvadipine and a pharmaceutically acceptable carrier, the pharmaceutical composition comprising an excess of (−)-nilvadipine relative to (+)-nilvadipine.

2. The pharmaceutical composition of claim 1 wherein the pharmaceutical composition has an enantiomeric excess of (−)-nilvadipine relative to (+)-nilvadipine of at least 90%.

3. The pharmaceutical composition of claim 1 wherein the pharmaceutical composition has an enantiomeric excess of (−)-nilvadipine relative to (+)-nilvadipine of at least 95%.

4. The pharmaceutical composition of claim 1 wherein the pharmaceutical composition has an enantiomeric excess of (−)-nilvadipine relative to (+)-nilvadipine of at least 98%.

5. The pharmaceutical composition of claim 1 wherein the pharmaceutical composition contains no detectible (+)-nilvadipine.

6. The pharmaceutical composition of any of claims 1-5 wherein the pharmaceutical composition is in unit dosage form.

7. The pharmaceutical composition of any of claims 1-5 wherein the pharmaceutical composition is in dosage unit form enclosed in hard or soft gelatin capsules or compressed into tablets.

8. The pharmaceutical composition of any of claims 1-5 wherein the pharmaceutical composition is in unit dosage form suitable for parenteral, oral or interperitoneal administration.

* * * * *